United States Patent
Kim et al.

(10) Patent No.: US 11,963,988 B2
(45) Date of Patent: Apr. 23, 2024

(54) LACTIC ACID BACTERIA AND USE THEREOF

(71) Applicants: University-Industry Cooperation Group of Kyung Hee University, Gyeonggi-do (KR); Navipharm Co., Ltd., Gyeonggi-do (KR)

(72) Inventors: Dong Hyun Kim, Seoul (KR); Myung Joo Han, Seoul (KR)

(73) Assignees: University-Industry Cooperation Group of Kyung Hee University, Gyeonggi-do (KR); Navipharm Co., Ltd., Gyeonggi-do (KR)

( * ) Notice: Subject to any disclaimer, the term of this patent is extended or adjusted under 35 U.S.C. 154(b) by 16 days.

(21) Appl. No.: 17/714,955

(22) Filed: Apr. 6, 2022

(65) Prior Publication Data

US 2022/0370523 A1 Nov. 24, 2022

Related U.S. Application Data

(63) Continuation of application No. 16/765,834, filed as application No. PCT/KR2018/014271 on Nov. 20, 2018, now Pat. No. 11,324,786.

(30) Foreign Application Priority Data

Nov. 20, 2017 (KR) .................. 10-2017-0155078
Nov. 19, 2018 (KR) .................. 10-2018-0142811

(51) Int. Cl.
*A61K 35/745* (2015.01)
*A23L 33/00* (2016.01)
(Continued)

(52) U.S. Cl.
CPC .......... *A61K 35/747* (2013.01); *A23L 33/125* (2016.08); *A23L 33/135* (2016.08);
(Continued)

(58) Field of Classification Search
CPC .................................................. A61K 35/745
See application file for complete search history.

(56) References Cited

U.S. PATENT DOCUMENTS

| | | |
|---|---|---|
| 2012/0201796 A1 | 8/2012 | Beasley et al. |
| 2015/0050254 A1 | 2/2015 | Kelly |
| 2016/0017378 A1 | 1/2016 | Kohn et al. |

FOREIGN PATENT DOCUMENTS

| | | | |
|---|---|---|---|
| JP | 2009-100692 A | 5/2009 |
| JP | 2011-517568 A | 6/2011 |

(Continued)

OTHER PUBLICATIONS

English machine translation from Korean of Lioing et al., WO 2017/130859 A1, 2017.*

(Continued)

*Primary Examiner* — Rosanne Kosson
(74) *Attorney, Agent, or Firm* — Wood, Phillips, Katz, Clark & Mortimer

(57) ABSTRACT

The present invention relates to the novel lactic acid bacteria *Lactobacillus mucosae* and *Bifidobacterium longum*, and specifically, to a composition comprising the novel lactic acid bacteria, the composition enabling the inhibition of the expression of the p16 protein, which is an aging factor, and the inhibition of inflammatory factors, thereby being useful in preventing and treating memory impairment, learning disabilities or mental disorders, and in preventing and treating inflammatory diseases.

6 Claims, 12 Drawing Sheets

Specification includes a Sequence Listing.

(51) Int. Cl.

| | |
|---|---|
| *A23L 33/125* | (2016.01) |
| *A23L 33/135* | (2016.01) |
| *A61K 35/747* | (2015.01) |
| *A61P 1/00* | (2006.01) |
| *A61P 25/22* | (2006.01) |
| *A61P 25/24* | (2006.01) |
| *A61P 25/28* | (2006.01) |
| *A61K 35/00* | (2006.01) |

(52) U.S. Cl.
CPC ............ *A23L 33/40* (2016.08); *A61K 35/745* (2013.01); *A61P 1/00* (2018.01); *A61P 25/22* (2018.01); *A61P 25/24* (2018.01); *A61P 25/28* (2018.01); *A23V 2002/00* (2013.01); *A23V 2400/533* (2023.08); *A61K 2035/11* (2013.01)

(56) References Cited

FOREIGN PATENT DOCUMENTS

| | | |
|---|---|---|
| JP | 2015-077133 A | 4/2015 |
| RU | 2378370 C2 | 1/2010 |
| WO | 2010-060722 A1 | 5/2010 |
| WO | 2013008039 A2 | 1/2013 |
| WO | 2013093561 A1 | 6/2013 |
| WO | 2017-134240 A1 | 8/2017 |

OTHER PUBLICATIONS

Office Action for corresponding JP Application No. 2020-527989.
Yu et al., "A novel srain of Lactobacilus mucosae isolated from a Gaotian villager improves in vitro and in vivo antioxidant as well as biological properties in a-galactose-induced aging mice", Journal of Dairy Science vol. 99, No. 2, p. 903-914, 2016.
International Search Report for corresponding PCT Application No. PCT/KR2018/014271 dated May 30, 2019.
First Office Action for corresponding KR Application No. 10-2021-0057549 dated May 27, 2021.
Search Report for corresponding EP Application No. 18878662.8 dated Apr. 23, 2021.
First Office Action for corresponding RU Application No. 2020116733 dated Jul. 29, 2021.
Di Cerbo A, et al. J Clin Pathol 2016;69:187-203. doi:10.1136/jclinpath-2015-202976.
I.G. Barbosa et al./ Neuroscience Letters 475 (2010) 95-98.
Cold Spring Harb Perspect Biol. 2009; 1:a001651.

* cited by examiner

LACTIC ACID BACTERIA AND USE THEREOF

TECHNICAL FIELD

The present disclosure relates to *Lactobacillus mucosae* and *Bifidobacterium longum* as novel lactic acid bacteria. Specifically, the present disclosure relates to a composition containing the novel lactic acid bacteria for inhibiting expression of p16 protein as an aging factor and inhibiting expression of an inflammatory factor, thereby being useful for prevention and treatment of memory impairment, learning disability or mental disorder, and for prevention and treatment of inflammatory diseases.

BACKGROUND ART

Among diseases caused by increase in elderly population, memory impairment including dementia is the most problematic. According to the annual report from the Central Dementia Center of the Ministry of Health and Welfare, one patient having dementia occurs every 12 minutes, and 650,000 people suffer from dementia. In particular, dementia which is known to occur mainly in older people in their 70s or older recently increasingly occurs in young people due to chronic disease, external injury, genetic factors, and poor lifestyle.

It may be difficult to cure the memory impairment including dementia. When memory impairment occurs, a lifelong pain and burden are imposed not only on the patient, but also on the patient's family. Thus, problems derived therefrom are at a serious level.

Further, commercially available dementia treatment agents are limited in use because of digestive system-related side effects thereof such as nausea, vomiting, loss of appetite, and, abdominal pain, and side effects thereof such as skin redness and itching.

From a result of a study using natural products, Korean Patent Application Publication No. 10-2016-0110767 discloses a food composition for improving memory using an extract of date plum. However, there are no studies on effective lactic acid bacteria that may treat memory impairment including dementia.

DISCLOSURE

Technical Problem

The present disclosure has been made in an effort to researching a treatment agent that may effectively restore memory power. The present inventors have identified that a novel lactic acid bacterium isolated from human feces has effects of improving memory power and reducing the anxiety behavior, and thus may be used for prevention and treatment of memory impairment, learning disability, and mental disorder. Thus, we have completed the present disclosure. Further, we have identified that the novel lactic acid bacteria isolated from human feces may suppress inflammatory factors and thus may be used for prevention and treatment of inflammatory disease, and memory impairment, learning disability, and mental disorder associated with the inflammatory factors.

Technical Solution

A purpose according to the present disclosure is to provide *Lactobacillus mucosae* and *Bifidobacterium longum* as novel lactic acid bacteria.

Another purpose according to the present disclosure is to provide a composition for preventing or treating memory impairment, learning disability, or mental disorder, the composition containing the novel lactic acid bacteria suppressing expression of a p16 protein as an aging factor.

Still another purpose according to the present disclosure is to provide a composition for preventing or treating inflammatory diseases, the composition containing the novel lactic acid bacteria.

Advantageous Effects

The novel lactic acid bacteria *Lactobacillus mucosae* NK41 and *Bifidobacterium longum* NK46 according to the present disclosure have the effect of suppressing expression of the p16 protein as the aging factor and have a memory recovery effect, and reduce the anxiety behavior. Therefore, the novel lactic acid bacteria according to the present disclosure may be used as a composition for preventing or treating the memory impairment, learning disability, or mental disorder.

Furthermore, the novel lactic acid bacteria according to the present disclosure have an effect of inhibiting an inflammatory response, and thus may be contained in a composition for preventing or treating inflammatory diseases, and is particularly effective for preventing and treating colitis.

(From left) Control group; Alzheimer's disease animal model; LM treated group; and BL treated group.

Figure 7:
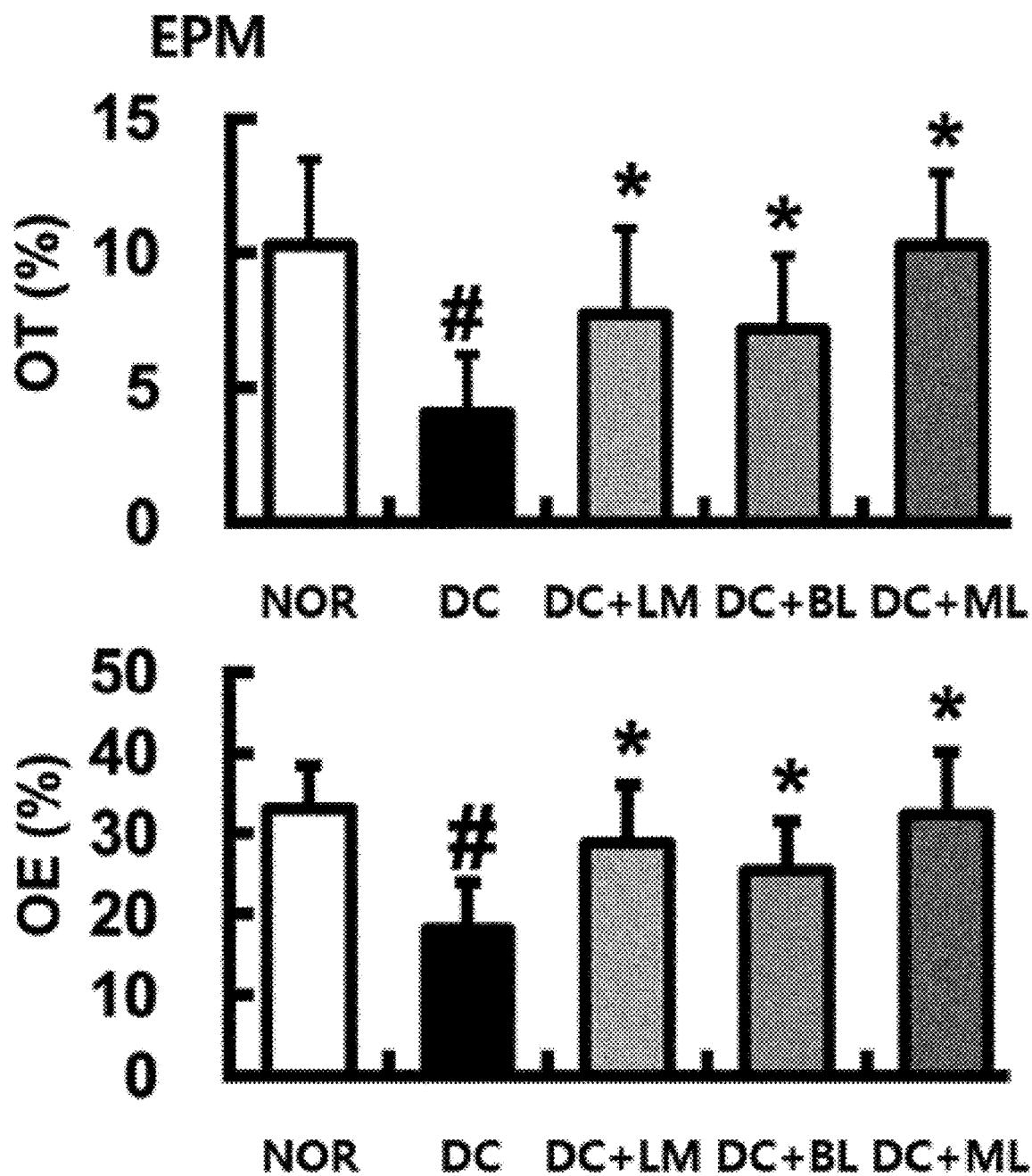

FIG. 7 shows a graph identifying that each of a time spent in an open arm (OT) and an open arm entry (OE) is restored to a level of a normal group (NOR) by administering the novel lactic acid bacterium *Lactobacillus mucosae* NK41 (LM) or *Bifidobacterium longum* NK46 (BL) to a depressed animal model.

Figure 8:
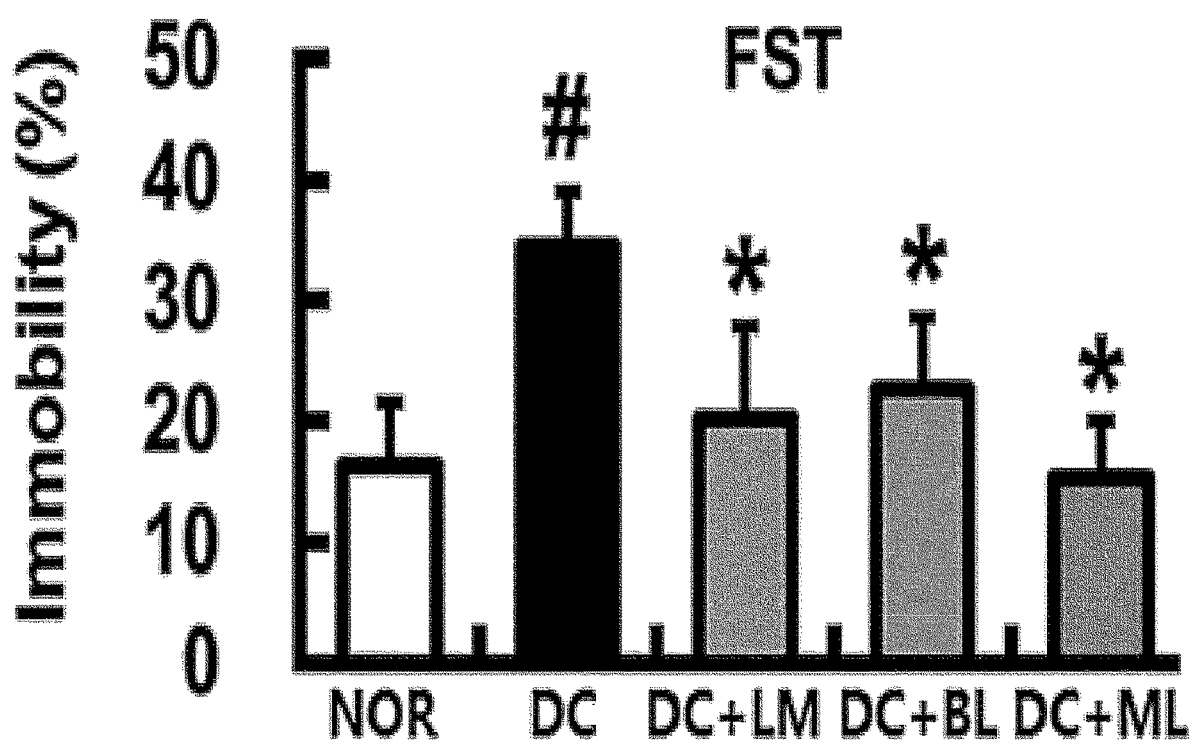

FIG. 8 shows a graph identifying that an immobility is reduced in a forced swimming test, resulting in reduction of anxiety behavior and depression symptom, by administering the novel lactic acid bacterium *Lactobacillus mucosae* NK41 (LM) or *Bifidobacterium longum* NK46 (BL) to a depressed animal model.

Figure 9:
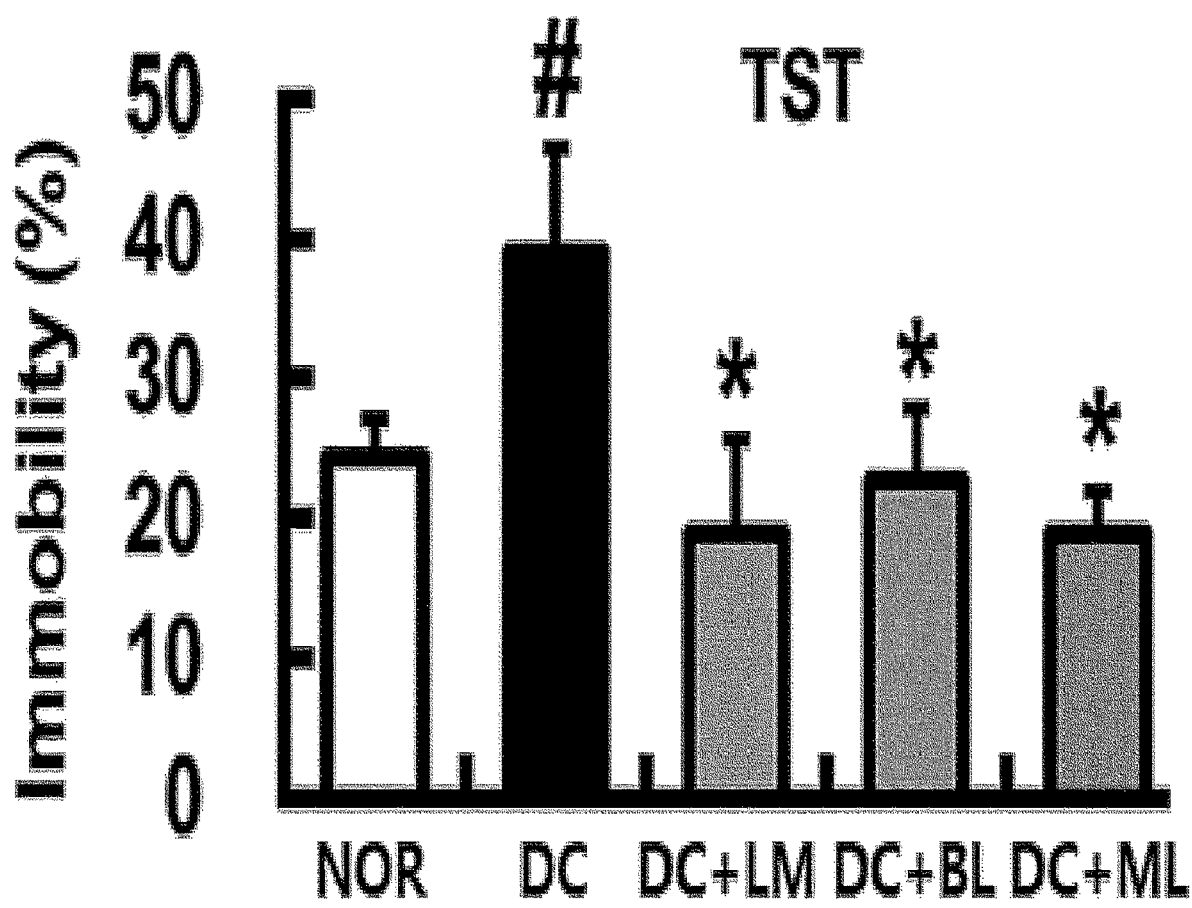

FIG. 9 shows a graph identifying that an immobility is reduced in a tail suspension test, resulting in reduction of anxiety behavior and depression symptom, by administering the novel lactic acid bacterium *Lactobacillus mucosae* NK41 (LM) or *Bifidobacterium longum* NK46 (BL) to a depressed animal model.

Figure 10:
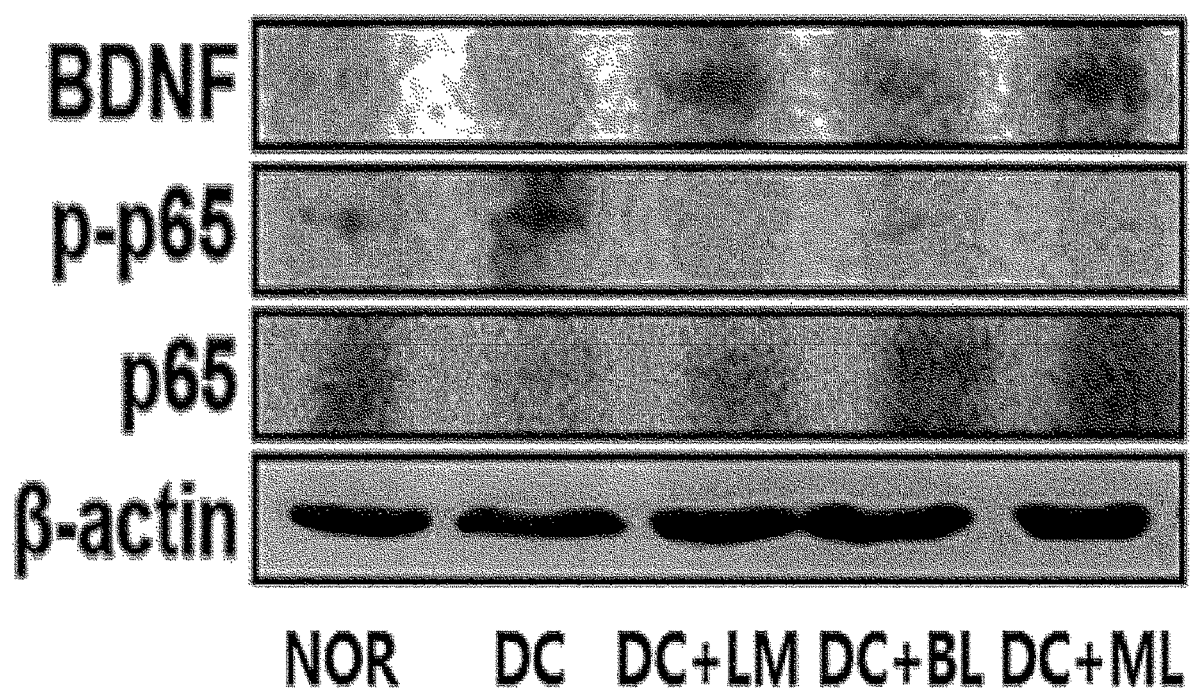

FIG. 10 is a diagram that identifies that activity of NF-kB in hippocampus is inhibited and the expression of brain derived neurotrophic factor (BDNF) increases, by administering the novel lactic acid bacterium *Lactobacillus mucosae* NK41 (LM) or *Bifidobacterium longum* NK46 (BL) to a depressed animal model.

Figure 11:
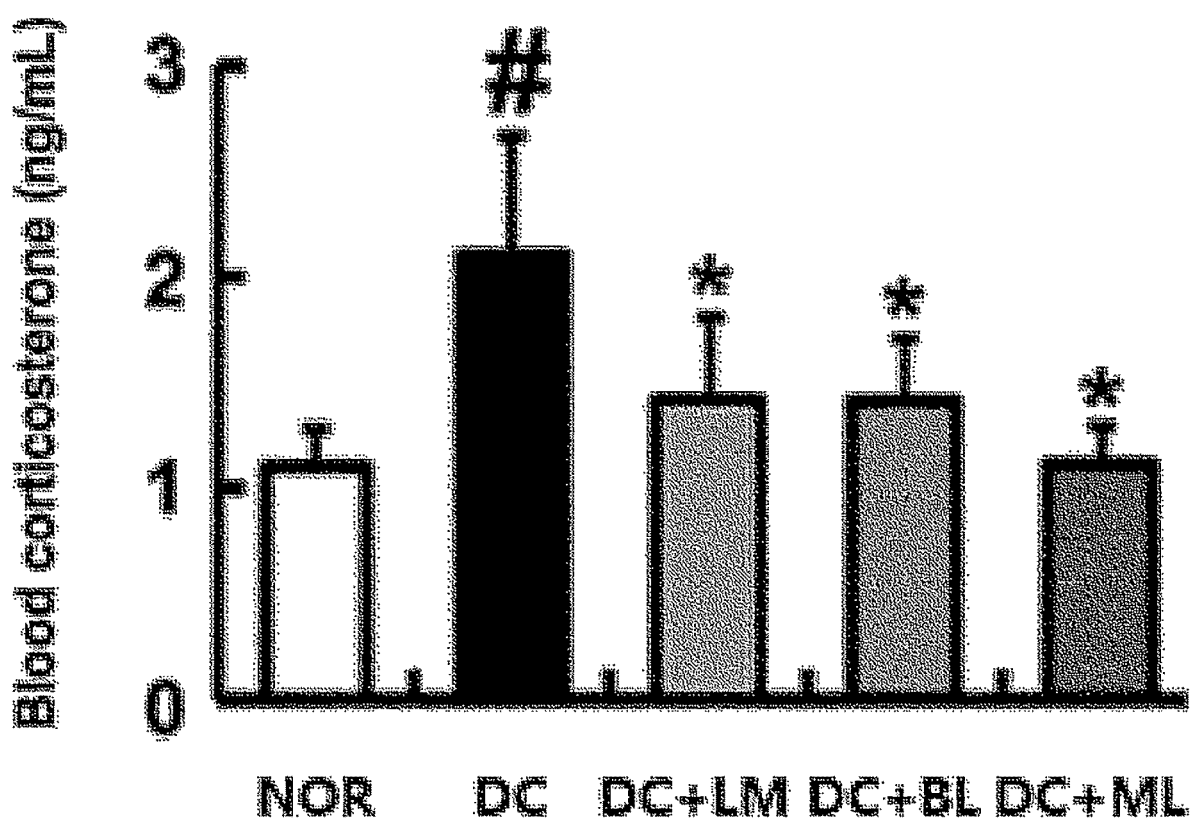

FIG. 11 is a graph identifying significant reduction in a level of corticosterone in a blood by administering the novel lactic acid bacterium *Lactobacillus mucosae* NK41 (LM) or *Bifidobacterium longum* NK46 (BL) to a depressed animal model.

Figure 12:
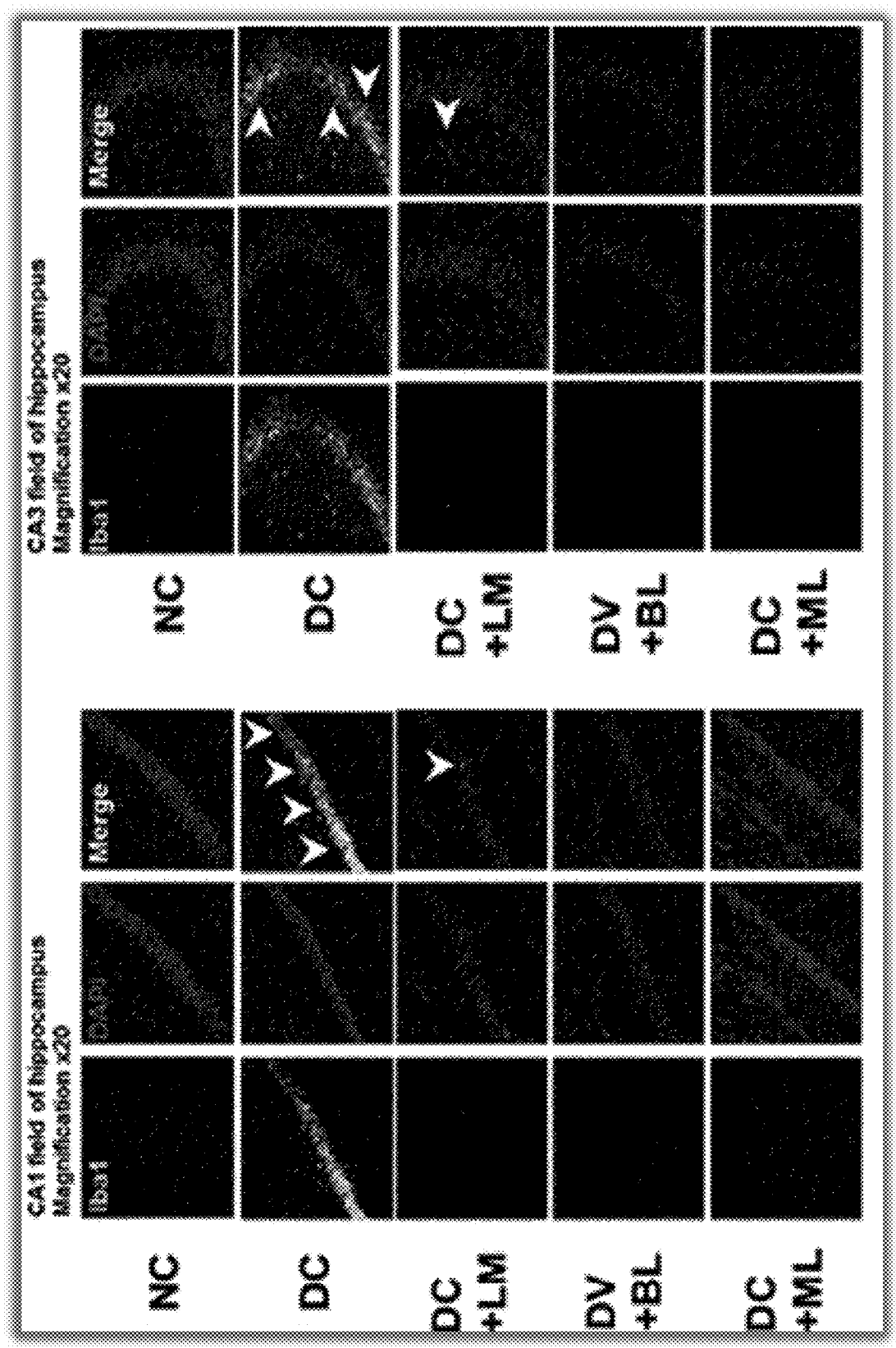

FIG. 12 is a diagram that identifies that Iba1-positive microglia activity decrease significantly, via administration of the novel lactic acid bacterium *Lactobacillus mucosae* NK41 (LM) or *Bifidobacterium longum* NK46 (BL) to a depressed animal model.

MODES OF THE INVENTION

In one aspect for achieving the purpose, the present disclosure provides *Lactobacillus mucosae* NK41 (Depository Organization: Korean Culture Center of Microorganisms, 45 Hongjenae 2ga-gil, Hongje-dong, Seodaemun-gu, Seoul, 120-861, Republic of Korea, Deposit Date: Aug. 4, 2017, Accession No: KCCM12091P).

*Lactobacillus mucosae* NK41 according to the present disclosure is a novel lactic acid bacterium of *Lactobacillus mucosae* isolated and identified from human feces.

A 16S rDNA base sequence for identification and classification of *Lactobacillus mucosae* NK41 according to the present disclosure is the same as SEQ ID NO: 1 as attached to the present specification. Therefore, *Lactobacillus mucosae* NK41 according to the present disclosure may contain 16S rDNA represented by SEQ ID NO: 1.

Referring to an analysis result of the 16S rDNA base sequence represented by the SEQ ID NO: 1, the 16S rDNA base sequence represented by the SEQ ID NO: 1 has 99% homology with known *Lactobacillus mucosae* strains, and thus has the highest molecular relationship with *Lactobacillus mucosae*. Therefore, the lactic acid bacterium is identified as *Lactobacillus mucosae*, is named as *Lactobacillus mucosae* NK41, and is deposited with the Korean Culture Center of Microorganisms on Aug. 4, 2017 (Accession No. KCCM12091P).

*Lactobacillus mucosae* NK41 according to the present disclosure is a Gram-positive bacterium, and a cell form thereof is *Bacilli*. More specifically, the physiological properties of *Lactobacillus mucosae* NK41 may be analyzed according to conventional methods in the art, and the results are shown in Table 2 below. Specifically, *Lactobacillus mucosae* NK41 may utilize, as carbon sources, L-arabinose, D-ribose, D-xylose, D-galactose, D-glucose, amygdalin, esculin, maltose, lactose, melibiose, sucrose, raffinose, gentiobiose, and gluconate.

In another aspect for achieving the purpose, the present disclosure provides *Bifidobacterium longum* NK46 (Depository Organization: Korean Culture Center of Microorganisms, 45 Hongjenae 2ga-gil, Hongje-dong, Seodaemun-gu, Seoul, 120-861, Republic of Korea, Deposit Date: Aug. 4, 2017, Accession No: KCCM12087P).

*Bifidobacterium longum* NK46 according to the present disclosure is a novel lactic acid bacterium of *Bifidobacterium longum* isolated and identified from human feces.

A 16S rDNA base sequence for identification and classification of *Bifidobacterium longum* NK46 according to the present disclosure is the same as SEQ ID NO: 2 attached to the present specification. Accordingly, *Bifidobacterium longum* NK46 according to the present disclosure may contain 16S rDNA represented by SEQ ID NO: 2.

Referring to an analysis result of the 16S rDNA base sequence represented by the SEQ ID NO: 2, the 16S rDNA base sequence represented by the SEQ ID NO: 2 has 99% homology with known *Bifidobacterium longum* strains, and has the highest molecular phylogenetic relationship with *Bifidobacterium longum*. Therefore, the lactic acid bacterium is identified as *Bifidobacterium longum*, named as *Bifidobacterium longum* NK46, and deposited with the Korean Culture Center of Microorganisms on Aug. 4, 2017 (Accession No. KCCM12087P).

*Bifidobacterium longum* NK46 according to the present disclosure is a Gram-positive bacterium, and a cell form thereof is *Bacilli*. The physiological properties of the *Bifidobacterium longum* NK46 may be analyzed according to conventional methods in the art, and the results are shown in Table 3 below. Specifically, *Bifidobacterium longum* NK46 may utilize, as carbon sources, L-arabinose, D-xylose, D-galactose, D-glucose, D-fructose, D-mannose, mannitol, sorbitol, α-methyl-D-glucoside, esculin, salicin, maltose, lactose, melibiose, sucrose, raffinose, and D-turanose.

In another aspect for achieving the purpose, the present disclosure provides a pharmaceutical composition for preventing or treating memory impairment, learning disability or mental disorder, the composition containing *Lactobacillus mucosae* NK41 KCCM12091P, *Bifidobacterium longum* NK46 KCCM12087P, or a mixture thereof.

"*Lactobacillus mucosae* NK41" according to the present disclosure is the same as described above.

Specifically, *Lactobacillus mucosae* NK41 contained in the pharmaceutical composition according to the present disclosure may be a live probiotic thereof, a heat killed probiotic thereof, a culture thereof, a lysate thereof, or an extract thereof. Any form of *Lactobacillus mucosae* NK41 that may achieve the prevention or treatment effect of memory impairment, learning disability, or mental disorder may be used without limitation.

"*Bifidobacterium longum* NK46" according to the present disclosure is the same as described above.

Specifically, the *Bifidobacterium longum* NK46 contained in the pharmaceutical composition according to the present disclosure may be a live probiotic thereof, a heat killed probiotic thereof, a culture thereof, a lysate thereof or an extract thereof. Any form of *Bifidobacterium longum* NK46 that may achieve the prevention or treatment effect of memory impairment, learning disability, or mental disorder may be used without limitation.

The term "culture" in the present disclosure refers to a substance obtained by culturing the lactic acid bacteria in a known liquid medium or solid medium, and is the concept including the novel lactic acid bacteria herein.

Memory impairment and learning disability according to the present disclosure may be any one or more selected from the group consisting of aging, Alzheimer's disease, schizophrenia, Parkinson's disease, Huntington's disease, Pick's disease, Creutzfeldt-Jakob disease, aging, head trauma, forgetfulness, memory power decrease, traumatic brain injury, epilepsy, hippocampal sclerosis, headache, cerebral senile disease, dementia, and memory loss.

In one embodiment according to the present disclosure, it is identified that when treating a nerve cell with *Lactobacillus mucosae* NK41 or *Bifidobacterium longum* NK46 together with stress hormone corticosterone, the activity of NF-kB, which is known to cause memory impairment such as Alzheimer's disease and learning disability is inhibited, and, at the same time, the expression of brain derived neurotrophic factor (BDNF) which is known to have a lowered expression level in the aging and dementia increases (Table 5). Further, in one embodiment according to the present disclosure, it is identified that when administering *Lactobacillus mucosae* NK41, *Bifidobacterium longum* NK46 or a mixture thereof to the aged animal model and the Alzheimer's disease animal model, a memory recovery effect is achieved, the expression of p16 as an aging factor in hippocampus is suppressed, the activity of NF-kB is suppressed, and the expression of brain derived neurotrophic factor is increased (Example 4). In particular, it is identified that the mixture of *Lactobacillus mucosae* NK41 and *Bifidobacterium longum* NK46 shows better effect than when *Lactobacillus mucosae* NK41 or *Bifidobacterium longum* NK46 is used alone. Thus, it is identified that the pharmaceutical composition containing the *Lactobacillus mucosae* NK41, *Bifidobacterium longum* NK46 or a mixture thereof may be useful for prevention and treatment of the memory impairment and learning disability.

Therefore, the pharmaceutical composition according to the present disclosure containing *Lactobacillus mucosae* NK41 KCCM12091P, *Bifidobacterium longum* NK46 KCCM12087P or a mixture thereof, may suppress the expression of aging factor p16.

The p16 is a representative aging factor protein expressed from the human CDKN2A gene. Thus, the aging is promoted as the expression of the p16 increases.

The mental disorder according to the present disclosure may be any one or more selected from the group consisting of anxiety, depressed symptoms, mood disorders, insomnia, delusional disorder, obsessive compulsive disorder, migraine, stress, cognitive disorder, and attention disorder.

In an embodiment according to the present disclosure, it is identified that stress-induced anxiety behavior is significantly reduced when *Lactobacillus mucosae* NK41, *Bifidobacterium longum* NK46, or a mixture thereof is administered to a stress-induced animal model (Table 8). Thus, it is identified that the pharmaceutical composition containing the *Lactobacillus mucosae* NK41, *Bifidobacterium longum* NK46, or a mixture thereof may be useful for the prevention and treatment of mental disorders.

In another aspect for achieving the purpose, the present disclosure provides a pharmaceutical composition for preventing or treating inflammatory disease, the composition containing *Lactobacillus mucosae* NK41 KCCM12091P, *Bifidobacterium longum* NK46 KCCM12087P or a mixture thereof.

"*Lactobacillus mucosae* NK41" and "*Bifidobacterium longum* NK46" according to the present disclosure are the same as described above.

Inflammatory diseases according to the present disclosure may be any one or more selected from the group consisting of arthritis, gout, hepatitis, asthma, obesity, keratitis, gastritis, enteritis, nephritis, colitis, diabetes, tuberculosis, bronchitis, pleurisy, peritonitis, spondylitis, pancreatitis, inflammatory pain, urethritis, cystitis, vaginitis, atherosclerosis, sepsis, burns, dermatitis, periodontitis, and gingivitis.

In one embodiment according to the present disclosure, it is identified that the inflammatory response is significantly inhibited when administering *Lactobacillus mucosae* NK41 or *Bifidobacterium longum* NK46 together with lipopolysaccharide as an inflammatory response inducing substance, to macrophage isolated from mouse (Table 4). Thus, it is identified that the pharmaceutical composition containing the *Lactobacillus mucosae* NK41 and *Bifidobacterium longum* NK46 may be useful for the prevention and treatment of inflammatory diseases.

Specifically, the inflammatory disease may be colitis.

In an embodiment according to the present disclosure, It is identified that when the *Lactobacillus mucosae* NK41, *Bifidobacterium longum* NK46 or a mixture thereof is administered to an animal model having colitis induced due to stress, a length of a large intestine as an index of colitis is restored to a normal level, and the expression and activity of an indicator of the colitis decreases (Table 6). Thus, it is identified that the pharmaceutical composition containing the *Lactobacillus mucosae* NK41, *Bifidobacterium longum* NK46, or a mixture thereof may be useful for the prevention and treatment of the inflammatory diseases, specifically, the colitis.

A pharmaceutical composition for the prevention or treatment of the memory impairment, learning disability or mental disorder according to the present disclosure, or a pharmaceutical composition for the prevention or treatment of inflammatory disease may be prepared in pharmaceutical formulations using methods well known in the art to provide rapid, sustained or delayed release of the active ingredient after the administration thereof to a mammal. In the preparation of the formulation, the pharmaceutical composition according to the present disclosure may additionally contain a pharmaceutically acceptable carrier within a range that does not inhibit the activity of the novel lactic acid bacteria.

The pharmaceutically acceptable carriers include, but are not limited to, those commonly used, such as lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, and the like. Further, the pharmaceutical composition according to the present disclosure may contain diluents or excipients such as fillers, extenders, binders, wetting agents, disintegrating agents, surfactants, and other pharmaceutically acceptable additives.

The dosage of the pharmaceutical composition according to the present disclosure should be a pharmaceutically effective amount. "Pharmaceutically effective amount" means an amount sufficient to prevent or treat the memory impairment, learning disability, mental disorder, or inflammatory disease at a reasonable benefit/risk ratio applicable to medical treatment. The effective dose level is variously selected by a person skilled in the art according to factors such as the formulation method, the patient's condition and weight, the patient's gender, age, disease severity, drug form, administration route and duration, excretion rate, and response sensitivity. The effective amount may vary depending on the route of treatment, the use of excipients, and the possibility of use with other agents, as recognized by those skilled in the art. However, for the desired effect, in the oral administration of the composition according to the present disclosure, the composition is generally administered to an adult at 0.0001 to 100 mg per 1 kg of a body weight per one day, preferably at 0.001 to 100 mg per 1 kg of a body weight per one day. The administration may be done once a day, and may be divided into several times. The dosage does not limit the scope of the present disclosure in any way.

The pharmaceutical composition for the prevention or treatment of memory impairment, learning disability or mental disorder according to the present disclosure, or the pharmaceutical composition for preventing or treating inflammatory disease, may be administered to mammals such as mice, livestock, and humans through various routes. Specifically, the pharmaceutical composition according to the present disclosure may be administered orally or parenterally (e.g., applied or injected intravenously, subcutaneously, or intraperitoneally). However, the oral administration is preferred. Solid preparations for oral administration may include powders, granules, tablets, capsules, soft capsules, pills, and the like. Liquid preparations for oral administration may include suspending agents, solutions, emulsions, syrups, aerosols, etc. In addition to water and liquid paraffin, which are commonly used as simple diluent, various excipients, such as wetting agents, sweeteners, fragrances, and preservatives, are contained therein. Formulations for parenteral administration are formulated in the form of external applications such as aqueous solutions, liquids, non-aqueous solvents, suspensions, emulsions, eye drops, eye ointments, syrups, suppositories, aerosols, etc. and sterile injection as sterilized according to conventional methods. Preferably, a pharmaceutical composition such as cream, gel, patch, spray, ointment, plaster, lotion, liniment agent, eye ointment, eye drop, pasta or cataplasma may be prepared and used. However, the present disclosure is not limited thereto. Formulations for topical administration may be anhydrous or aqueous, depending on the clinical regimen. Propylene glycol, polyethylene glycol, vegetable oil such as olive oil, injectable esters, such as ethyl oleate may be used as non-aqueous solvents, and suspensions. As a base for suppositories, witepsol, macrogol, tween 61, cacao butter, laurin butter, glycerogelatin, and the like may be used.

In another aspect for achieving the purpose, the present disclosure provides a method for preventing or treating memory impairment, learning disability or mental disorder, comprising administering *Lactobacillus mucosae* NK41, *Bifidobacterium longum* NK46, or a mixture thereof to a subject.

The terms "*Lactobacillus mucosae* NK41", "*Bifidobacterium longum* NK46", "administration", "memory impairment, learning disability or mental disorder" in the present disclosure are the same as described above.

The subject refers to an animal, and may be a mammal capable of receiving a beneficial effect via treatment with the novel lactic acid bacteria according to the present disclosure. Preferred examples of such subjects include primates, such as humans. In addition, subjects having expression of the p16 protein as the aging factor, symptoms of memory impairment, learning disability, or mental disorder, and subjects having risks of having such symptoms may be included in the subjects herein.

In another aspect for achieving the purpose, the present disclosure provides a method for treating or preventing inflammatory diseases, comprising administering *Lactobacillus mucosae* NK41, *Bifidobacterium longum* NK46 or a mixture thereof to a subject.

In the present disclosure, the terms "*Lactobacillus mucosae* NK41" and "*Bifidobacterium longum* NK46", "administration" and "inflammatory" are the same as described above.

The subject refers to an animal, and may be a mammal capable of receiving a beneficial effect via treatment with the novel lactic acid bacteria according to the present disclosure. Preferred examples of such subjects include primates, such as humans. These subjects include all subjects having increased myeloperoxidase activity, increased expression levels of cytokines of TNF-$\alpha$ and IL-17, or increased NF-kB activity or COX-2 activity. Furthermore, all subjects having an inflammatory symptom or a risk of having such a symptom may be included therein. Specifically, the subject may be a subject having a symptom of colitis, but is not limited thereto.

In another aspect, the present disclosure provides a health functional food for preventing or alleviating the memory impairment, learning disability, or mental disorder, the food containing *Lactobacillus mucosae* NK41 KCCM12091P, *Bifidobacterium longum* NK46 KCCM12087P or a mixture thereof.

In another aspect, the present disclosure provides a health functional food for preventing or alleviating the inflammatory disease, the food containing *Lactobacillus mucosae* NK41 KCCM12091P, *Bifidobacterium longum* NK46 KCCM12087P or a mixture thereof.

The terms "*Lactobacillus mucosae* NK41" and "*Bifidobacterium longum* NK46", "administration" and "memory impairment, learning disability or mental disorder" and "inflammatory disease" according to the present disclosure are the same as described above.

The health functional food emphasizes the bio-regulatory function of the food. The health functional food has a value added to act and express for a specific purpose using physical, biochemical, and biotechnological methods. The components of these health functional foods are designed and processed so as to sufficiently exert, to the living body, the body control functions related to bio-defense and control of body rhythm, prevention, and recovery of diseases. Food-acceptable food additives or sweeteners, or functional raw materials may be contained therein.

When *Lactobacillus mucosae* NK41 or *Bifidobacterium longum* NK46 according to the present disclosure is contained in the health functional food (or health functional beverage additive), the novel lactic acid bacteria may be added as it is or may be used with other foods or food ingredients, or may be suitably used according to conventional methods. An added amount of the *Lactobacillus mucosae* NK41 or *Bifidobacterium longum* NK46 may be appropriately determined according to the purpose of use thereof (prevention, health or improvement, therapeutic treatment).

The health functional foods include various nutrients, vitamins, minerals (electrolytes), flavors such as synthetic flavors and natural flavors, colorants, and enhancers (cheese, chocolate, etc.), pectic acid and salts thereof, organic acids, protective colloid thickeners, pH adjusting agents, stabilizers, preservatives, glycerin, alcohol, carbonated agents used in carbonated beverages, and the like. Further, the health functional foods according to the present disclosure may contain flesh for the production of fruit and vegetable beverages. These components may be used alone or in combination with each other. Contents of these additives may be generally selected from a range of 0.001 to 50 parts by weight based on a total weight of the composition.

There are no particular restrictions on the types of the health functional foods. Foods to which the *Lactobacillus mucosae* NK41 or *Bifidobacterium longum* NK46 may be added may include sausage, meat, bread, chocolate, snacks, candy, confectionery, ramen, pizza, other noodles, gums, dairy products containing ice cream, various soups, beverages, teas, drinks, alcoholic beverages, vitamin complexes, and the like. When the food is formulated into a beverage, liquid components added thereto in addition to the novel lactic acid bacteria may include, as in the ordinary beverages, various flavoring agents or natural carbohydrates but may not be limited thereto. The natural carbohydrates as described above comprise monosaccharides (e.g., glucose, fructose, etc.), disaccharides (e.g., maltose, sucrose, etc.) and polysaccharides (e.g., conventional sugars such as dextrin, cyclodextrin, etc.), and sugar alcohols such as xylitol, sorbitol, erythritol, etc.

The numerical values as described in the present specification should be interpreted as including up to an equivalent range, unless otherwise specified.

EXAMPLES

Hereinafter, a preferred embodiment is provided to aid understanding according to the present disclosure. However, the following examples are only provided for the skilled person to the art to more easily understand the present disclosure, and the contents according to the present disclosure are not limited thereto.

Example 1: Isolation and Identification of Lactic Acid Bacteria (1) Isolation of Lactic Acid Bacteria from Human Feces Human feces were suspended in GAM broth (Nissui Pharmaceutical, Japan). Subsequently, a supernatant was taken therefrom and was transplanted into BL agar medium (Nissui Pharmaceutical, Japan), and then was subjected to anaerobic culture at 37° C. for about 48 hours to form colonies. Then, the strains were isolated.

(2) Isolation of Lactic Acid Bacteria from Kimchi

Chinese cabbage kimchi, radish kimchi or green onion kimchi were crushed respectively, and a crushed supernatant was taken therefrom, and then was transplanted into MRS agar medium (Difco, USA) and was subjected to anaerobic culture at 37° C. for about 48 hours to form colonies. Then, the strains were isolated.

(3) Identification of Isolated Lactic Acid Bacteria

Physiological characteristics and 16S rDNA sequences of the strains isolated from human feces or kimchi were analyzed to identify the species of the strain. Then, the strain name was assigned thereto. The assigned strain names of the lactic acid bacteria are shown in Table 1 below. Specifically, the lactic acid bacteria isolated from kimchi included *Lactobacillus plantarum* 5 types (identification numbers 1 to 5 of Table 1), *Lactobacillus brevis* 5 types (identification numbers 6 to 10 of Table 1), *Lactobacillus sakei* 5 types (identification numbers 11 to 15 of Table 1), and *Lactobacillus curvatus* 5 types (identification numbers 16 to 20 of Table 1). Lactic acid bacteria isolated from human feces included *Lactobacillus rhamnosus* 5 types (identification numbers 21 to 25 of Table 1), *Lactobacillus plantarum* 5 types (identification numbers 26 to 30 of Table 1), *Lacto-* *bacillus reuteri* 5 types (identification numbers 31 to 35 in Table 1), *Lactobacillus johnsonii* 4 types (identification numbers 36 to 39 in Table 1), *Lactobacillus mucosae* 3 types (identification numbers 40 to 42 in Table 1), *Bifidobacterium adolescentis* 3 types (identification numbers 43 to 45 of Table 1), and *Bifidobacterium longum* 5 types (identification numbers 46 to 50 of Table 1).

TABLE 1

| ID No. | Strain name |
|---|---|
| 1 | *Lactobacillus plantarum* NK1 |
| 2 | *Lactobacillus plantarum* NK2 |
| 3 | *Lactobacillus plantarum* NK3 |
| 4 | *Lactobacillus plantarum* NK4 |
| 5 | *Lactobacillus plantarum* NK5 |
| 6 | *Lactobacillus brevis* NK6 |
| 7 | *Lactobacillus brevis* NK7 |
| 8 | *Lactobacillus brevis* NK8 |
| 9 | *Lactobacillus brevis* NK9 |
| 10 | *Lactobacillus brevis* NK10 |
| 11 | *Lactobacillus sakei* NK11 |
| 12 | *Lactobacillus sakei* NK12 |
| 13 | *Lactobacillus sakei* NK13 |
| 14 | *Lactobacillus sakei* NK14 |
| 15 | *Lactobacillus sakei* NK15 |
| 16 | *Lactobacillus curvatus* NK16 |
| 17 | *Lactobacillus curvatus* NK17 |
| 18 | *Lactobacillus curvatus* NK18 |
| 19 | *Lactobacillus curvatus* NK19 |
| 20 | *Lactobacillus curvatus* NK20 |
| 21 | *Lactobacillus rhamnosus* NK21 |
| 22 | *Lactobacillus rhamnosus* NK22 |
| 23 | *Lactobacillus rhamnosus* NK23 |
| 24 | *Lactobacillus rhamnosus* NK24 |
| 25 | *Lactobacillus rhamnosus* NK25 |
| 26 | *Lactobacillus plantarum* NK26 |
| 27 | *Lactobacillus plantarum* NK27 |
| 28 | *Lactobacillus plantarum* NK28 |
| 29 | *Lactobacillus plantarum* NK29 |
| 30 | *Lactobacillus plantarum* NK30 |
| 31 | *Lactobacillus reuteri* NK31 |
| 32 | *Lactobacillus reuteri* NK32 |
| 33 | *Lactobacillus reuteri* NK33 |
| 34 | *Lactobacillus reuteri* NK34 |
| 35 | *Lactobacillus reuteri* NK35 |
| 36 | *Lactobacillus johnsonii* NK36 |
| 37 | *Lactobacillus johnsonii* NK37 |
| 38 | *Lactobacillus johnsonii* NK38 |
| 39 | *Lactobacillus johnsonii* NK39 |
| 40 | *Lactobacillus mucosae* NK40 |
| 41 | *Lactobacillus mucosae* NK41 |
| 42 | *Lactobacillus mucosae* NK42 |
| 43 | *Bifidobacterium adolescentis* NK43 |
| 44 | *Bifidobacterium adolescentis* NK44 |
| 45 | *Bifidobacterium adolescentis* NK45 |
| 46 | *Bifidobacterium longum* NK46 |
| 47 | *Bifidobacterium longum* NK47 |
| 48 | *Bifidobacterium longum* NK48 |
| 49 | *Bifidobacterium longum* NK49 |
| 50 | *Bifidobacterium longum* NK50 |

(4) Physiological Properties of Novel Lactic Acid Bacterium *Lactobacillus mucosae* NK41

Among the strains as described in Table 1, *Lactobacillus mucosae* NK41 (Accession No. KCCM12091P) was identified as Gram-positive *Bacilli*. Further, 16S rDNA of *Lactobacillus mucosae* NK41 had a base sequence represented by SEQ ID NO: 1. When analyzing the 16S rDNA base sequence of *Lactobacillus mucosae* NK41 using BLAST search, it was identified that *Lactobacillus mucosae* strain having the same 16S rDNA base sequence was not found, and the 16S rDNA base sequence of *Lactobacillus mucosae* NK41 had 99% homology with the 16S rDNA sequence of the known *Lactobacillus mucosae* strain.

Carbon source utilization among the physiological properties of *Lactobacillus mucosae* NK41 was analyzed via a sugar fermentation test using an API 50 CHL kit. The results are shown in Table 2 below. In the following Table 2, "+" indicates a case where the carbon source utilization is positive, and "−" indicates a case where the carbon source utilization is negative.

TABLE 2

| Carbon source | NK41 | Carbon source | NK41 |
| --- | --- | --- | --- |
| CONTROL | − | Esculin | + |
| Glycerol | − | Salicin | − |
| Erythritol | − | Cellobiose | − |
| D-arabinose | − | Maltose | + |
| L-arabinose | + | Lactose | ± |
| D-ribose | + | Melibiose | ± |
| D-xylose | + | Sucrose | + |
| L-xylose | − | Trehalose | − |
| D-adonitol | − | Inulin | − |
| Methyl-BD-Xylopyranoside | − | Melizitose | − |
| | | Raffinose | + |
| D-galactose | ± | Starch | − |
| D-glucose | + | Glycogen | − |
| D-fructose | − | Xylitol | − |
| D-mannose | − | Gentiobiose | ± |
| L-sorbose | − | D-turanose | + |
| Rhamnosus | − | D-lyxose | − |
| Dulcitol | − | D-tagatose | − |
| Inositol | − | L-fucose | − |
| Sorbitol | − | D-arabitol | − |
| α-methyl-D-mannoside | − | L-arabitol | − |
| α-methyl-D-glucoside | ± | Gluconate | ± |
| N-acetyl-glucosamine | − | 2-keto-gluconate | − |
| Amygdalin | ± | | |
| Arbutin | − | 5-keto-gluconate | − |

(5) Physiological Properties of Novel Lactic Acid Bacterium *Bifidobacterium longum* NK46

Among the strains described in Table 1, *Bifidobacterium longum* NK46 (Accession No. KCCM12087P) was identified as Gram-positive *Bacilli*. Further, the 16S rDNA of *Bifidobacterium longum* NK46 had a base sequence represented by SEQ ID NO: 2. When analyzing the 16S rDNA base sequence of *Bifidobacterium longum* NK46 using BLAST search, it was identified that *Bifidobacterium longum* strain having the same 16S rDNA base sequence was not found, and the 16S rDNA base sequence of *Bifidobacterium longum* NK46 had 99% homology with the 16S rDNA sequence of the known *Bifidobacterium longum* strain.

The carbon source utilization among the physiological properties of *Bifidobacterium longum* NK46 was analyzed via a sugar fermentation test using an API 50 CHL kit. The result is shown in the following Table 3. In the following Table 3, "+" represents a case where carbon source utilization is positive, and "−" represents a case where carbon source utilization is negative.

TABLE 3

| Carbon source | NK46 | Carbon source | NK46 |
| --- | --- | --- | --- |
| CONTROL | − | Esculin | + |
| Glycerol | − | Salicin | + |
| Erythritol | − | Cellobiose | − |
| D-arabinose | − | Maltose | + |
| L-arabinose | + | Lactose | − |
| D-ribose | − | Melibiose | + |
| D-xylose | + | Sucrose | + |
| L-xylose | − | Trehalose | − |
| D-adonitol | − | Inulin | − |
| Methyl-BD-Xylopyranoside | − | Melizitose | − |
| | | Raffinose | + |

TABLE 3-continued

| Carbon source | NK46 | Carbon source | NK46 |
| --- | --- | --- | --- |
| D-galactose | + | Starch | − |
| D-glucose | + | Glycogen | − |
| D-fructose | + | Xylitol | − |
| D-mannose | + | Gentiobiose | − |
| L-sorbose | − | D-turanose | + |
| Rhamnosus | − | D-lyxose | − |
| Dulcitol | − | D-tagatose | − |
| Inositol | + | L-fucose | − |
| Sorbitol | + | D-arabitol | − |
| α-methyl-D-mannoside | − | L-arabitol | − |
| α-methyl-D-glucoside | ± | Gluconate | − |
| N-acetyl-glucosamine | − | 2-keto-gluconate | − |
| Amygdalin | − | | |
| Arbutin | − | 5-keto-gluconate | − |

Example 2: Comparison of Isolated Lactic Acid Bacteria Activity (1) Antioxidant Activity (In Vitro)

DPPH (2,2-diphenyl-1-picrylhydrazyl) was dissolved in ethanol to reach a concentration of 0.2 mM to prepare a DPPH solution. A suspension of lactic acid bacteria ($1 \times 10^6$ CFU/mL) or a vitamin C solution (1 g/mL) was added to 0.1 mL of the DPPH solution and cultured at 37° C. for 20 minutes. The culture solution was centrifuged for 5 minutes at 3,000 rpm to obtain a supernatant. Then, the absorbance of the supernatant at 517 nm was measured to calculate the antioxidant activity of the isolated lactic acid bacteria. Antioxidant activity for each lactic acid bacterium is shown in Table 4 below.

(2) Measurement of Inflammation Indicator in Macrophage 2 ml of sterile 4% thioglycolate was administered to an abdominal cavity of C57BL/6 mouse (male, 6 weeks old 20 to 23 g). After 96 hours, the mouse was anesthetized and 8 ml of RPMI 1640 medium was administered to the abdominal cavity of the mouse. After 5 to 10 minutes, an RPMI medium (macrophage) in the abdominal cavity of the mouse was extracted, centrifuged for 10 minutes at 1,000 g, and washed twice with RPMI 1640 medium again. The macrophages were placed in 24-well plates at the number of $0.5 \times 10^6$ per well. The macrophages were treated with the isolated lactic acid bacteria (final treatment concentration: $1 \times 10^4$ cfu/ml, hereinafter, the same treatment concentration being applied) and the inflammatory response inducing substance lipopolysaccharide (LPS) for 2 hours or 24 hours, and then supernatant and cells were obtained. The obtained cells were placed in an RIPA buffer (Gibco) and homogenized. Cytokine expression levels of TNF-α and IL-10 were measured in a culture supernatant treated for 24 hours using an immunoblotting method. The expression levels of p65 (NF-kB), p-p65 (phosphor-NF-kB) and β were measured in the cells obtained by treatment for 2 hours using an immunoblotting method. The expression level of the inflammation indicator for each lactic acid bacterium is shown in Table 4 below.

(In activity measurements of Table 4: +++ refers to >90% (very strong); ++ refers to >60 to 90% (strong); + refers to >20 to 60% (weak); − refers to <20% (ineffective), the same indication being applied to Table 5)

TABLE 4

| ID No. | Strain name | Antioxidant activity | TNF-α Inhibition | IL-10 Expression level increase | NF-kB Inhibition |
|---|---|---|---|---|---|
| 1 | Lactobacillus plantarum NK1 | + | + | + | + |
| 2 | Lactobacillus plantarum NK2 | + | ++ | + | + |
| 3 | Lactobacillus plantarum NK3 | +++ | +++ | +++ | +++ |
| 4 | Lactobacillus plantarum NK4 | + | + | + | ++ |
| 5 | Lactobacillus plantarum NK5 | ++ | ++ | ++ | ++ |
| 6 | Lactobacillus brevis NK6 | + | + | + | + |
| 7 | Lactobacillus brevis NK7 | + | + | + | + |
| 8 | Lactobacillus brevis NK8 | + | + | + | + |
| 9 | Lactobacillus brevis NK9 | + | + | + | + |
| 10 | Lactobacillus brevis NK10 | − | + | + | + |
| 11 | Lactobacillus sakei NK11 | + | + | + | + |
| 12 | Lactobacillus sakei NK12 | − | ++ | + | + |
| 13 | Lactobacillus sakei NK13 | − | ++ | ++ | + |
| 14 | Lactobacillus sakei NK14 | − | + | + | + |
| 15 | Lactobacillus sakei NK15 | + | + | + | + |
| 16 | Lactobacillus curvatus NK16 | + | + | + | + |
| 17 | Lactobacillus curvatus NK17 | + | + | + | + |
| 18 | Lactobacillus curvatus NK18 | + | + | + | + |
| 19 | Lactobacillus curvatus NK19 | + | + | + | + |
| 20 | Lactobacillus curvatus NK20 | + | + | + | + |
| 21 | Lactobacillus rhamnosus NK21 | + | + | + | + |
| 22 | Lactobacillus rhamnosus NK22 | + | + | + | + |
| 23 | Lactobacillus rhamnosus NK23 | + | + | + | + |
| 24 | Lactobacillus rhamnosus NK24 | ++ | + | + | + |
| 25 | Lactobacillus rhamnosus NK25 | ++ | ++ | ++ | ++ |
| 26 | Lactobacillus plantaram NK26 | + | + | + | + |
| 27 | Lactobacillus plantaram NK27 | + | + | + | + |
| 28 | Lactobacillus plantaram NK28 | + | + | + | + |
| 29 | Lactobacillus plantaram NK29 | + | + | + | + |
| 30 | Lactobacillus plantaram NK30 | + | + | + | + |
| 31 | Lactobacillus reuteri NK31 | + | + | + | + |
| 32 | Lactobacillus reuteri NK32 | ++ | ++ | ++ | ++ |
| 33 | Lactobacillus reuteri NK33 | +++ | ++ | ++ | ++ |
| 34 | Lactobacillus reuteri NK34 | + | + | + | + |
| 35 | Lactobacillus reuteri NK35 | + | + | + | + |
| 36 | Lactobacillus johnsonii NK36 | ++ | ++ | ++ | + |
| 37 | Lactobacillus johnsonii NK37 | ++ | ++ | ++ | ++ |
| 38 | Lactobacillus johnsonii NK38 | + | + | + | + |
| 39 | Lactobacillus johnsonii NK39 | + | + | + | + |
| 40 | Lactobacillus mucosae NK40 | ++ | ++ | ++ | ++ |
| 41 | Lactobacillus mucosae NK41 | ++ | ++ | +++ | +++ |
| 42 | Lactobacillus mucosae NK42 | + | + | + | + |
| 43 | Bifidobacterium adolescentis NK43 | + | + | + | + |
| 44 | Bifidobacterium adolescentis NK44 | ++ | ++ | ++ | ++ |
| 45 | Bifidobacterium adolescentis NK45 | + | + | + | + |
| 46 | Bifidobacterium longum NK46 | +++ | ++ | +++ | +++ |
| 47 | Bifidobacterium longum NK47 | ++ | ++ | ++ | ++ |
| 48 | Bifidobacterium longum NK48 | + | + | + | + |
| 49 | Bifidobacterium longum NK49 | +++ | +++ | +++ | +++ |
| 50 | Bifidobacterium longum NK50 | + | + | + | + |

(3) Expression Effect of ZO-1 Protein of Caco2 Cell

The colorectal cancer cells, Caco2 cells, were obtained from a Korean cell line bank and were incubated in RPMI 1640 medium for 48 hours, and then the Caco2 cells were dispensed into 12-well plates in an amount of $2\times10^6$ per well. Each well was treated with 1 μg of LPS alone, or treated with 1 μg of LPS and $1\times10^4$ CFU of the lactic acid bacteria and then was cultured for 24 hours. Thereafter, the cells cultured in each well were collected therefrom, and the expression level of ZO-1 as a tight junction protein was measured using an immunoblotting method. The expression level of ZO-1 for each lactic acid bacterium is shown in Table 5 below.

(4) Brain Derived Neurotrophic Factor (BDNF) Expression Effect and NF-kB Activity Effect on SH-SY5Y Cells The nerve cells SH-SY5Y cells were obtained from a Korean cell line bank and cultured in DMEM medium with 10% FBS and 1% antibiotics added thereto, and dispensed into 12-well plates at $2\times10^6$ cells per well. Then, the lactic acid bacteria ($1\times10^4$ CFU/mL) and corticosterone at a concentration of 300 mg/mL were added to each well, followed by incubation. Then, the expression levels of NF-kB (p65, p-p65) and brain derived neurotrophic factor (BDNF) were measured using an immunoblotting method. The BDNF expression level and NF-kB activity level for each lactic acid bacterium are as shown in Table 5 below.

TABLE 5

| ID No. | Strain name | ZO-1 Expression level increase | BDNF Expression level increase | NF-kB Activity inhibition |
|---|---|---|---|---|
| 1 | Lactobacillus plantarum NK1 | + | + | + |
| 2 | Lactobacillus plantarum NK2 | + | + | + |
| 3 | Lactobacillus plantarum NK3 | ++ | + | ++ |
| 4 | Lactobacillus plantarum NK4 | + | + | + |
| 5 | Lactobacillus plantarum NK5 | ++ | + | ++ |
| 6 | Lactobacillus brevis NK6 | + | + | + |
| 7 | Lactobacillus brevis NK7 | + | + | + |
| 8 | Lactobacillus brevis NK8 | + | + | + |
| 9 | Lactobacillus brevis NK9 | + | + | + |
| 10 | Lactobacillus brevis NK10 | − | − | − |
| 11 | Lactobacillus sakei NK11 | + | + | + |
| 12 | Lactobacillus sakei NK12 | − | − | − |
| 13 | Lactobacillus sakei NK13 | + | + | + |
| 14 | Lactobacillus sakei NK14 | + | + | + |
| 15 | Lactobacillus sakei NK15 | + | + | + |
| 16 | Lactobacillus curvatus NK16 | + | + | + |
| 17 | Lactobacillus curvatus NK17 | + | + | + |
| 18 | Lactobacillus curvatus NK18 | + | + | + |
| 19 | Lactobacillus curvatus NK19 | + | + | + |
| 20 | Lactobacillus curvatus NK20 | + | + | + |
| 21 | Lactobacillus rhamnosus NK21 | + | − | + |
| 22 | Lactobacillus rhamnosus NK22 | + | − | + |
| 23 | Lactobacillus rhamnosus NK23 | + | − | + |
| 24 | Lactobacillus rhamnosus NK24 | ++ | + | ++ |
| 25 | Lactobacillus rhamnosus NK25 | + | + | ++ |
| 26 | Lactobacillus plantarum NK26 | + | + | + |
| 27 | Lactobacillus plantarum NK27 | + | + | + |
| 28 | Lactobacillus plantarum NK28 | + | + | + |
| 29 | Lactobacillus plantarum NK29 | + | + | + |
| 30 | Lactobacillus plantarum NK30 | + | + | + |
| 31 | Lactobacillus reuteri NK31 | + | + | + |
| 32 | Lactobacillus reuteri NK32 | ++ | + | ++ |
| 33 | Lactobacillus reuteri NK33 | ++ | ++ | ++ |
| 34 | Lactobacillus reuteri NK34 | + | + | + |
| 35 | Lactobacillus reuteri NK35 | + | + | + |
| 36 | Lactobacillus johnsonii NK36 | + | ++ | + |
| 37 | Lactobacillus johnsonii NK37 | ++ | + | ++ |
| 38 | Lactobacillus johnsonii NK38 | + | + | + |
| 39 | Lactobacillus johnsonii NK39 | + | − | + |
| 40 | Lactobacillus mucosae NK40 | ++ | + | ++ |
| 41 | Lactobacillus mucosae NK41 | ++ | ++ | +++ |
| 42 | Lactobacillus mucosae NK42 | + | + | + |
| 43 | Bifidobacterium adolescentis NK43 | + | + | + |
| 44 | Bifidobacterium adolescentis NK44 | ++ | ++ | ++ |
| 45 | Bifidobacterium adolescentis NK45 | + | + | + |
| 46 | Bifidobacterium longum NK46 | ++ | ++ | +++ |
| 47 | Bifidobacterium longum NK47 | + | ++ | ++ |
| 48 | Bifidobacterium longum NK48 | + | + | + |
| 49 | Bifidobacterium longum NK49 | + | + | ++ |
| 50 | Bifidobacterium longum NK50 | + | + | + |

(5) Test Result

When evaluating the activity of isolated lactic acid bacteria, it was identified that the novel lactic acid bacteria *Lactobacillus mucosae* NK41 and *Bifidobacterium longum* NK46 among the isolated lactic acid bacteria increased the expression level of the tight junction protein ZO-1, while exhibiting the excellent antioxidant activity and anti-inflammatory effect. In particular, it was identified that the novel lactic acid bacteria *Lactobacillus mucosae* NK41 and *Bifidobacterium longum* NK46 inhibited the activity of NF-kB which is known to cause aging-related diseases, such as Alzheimer's disease, and, at the same time, increased expression of brain derived neurotrophic factor that produces brain nerves that decrease in the aging and dementia (Table 4 and Table 5).

Example 3: Anti-Inflammatory and Colitis Reducing Effects of Novel Lactic Acid Bacteria (1) Preparation of Colitis Animal Model and Administration of Lactic Acid Bacteria Thereto 6 C57BL/6 mice (male, 21 to 23 g, 6 weeks old) formed one group which was adapted to a test room for 1 week. One group was used as a normal group, and the other group was treated with 2,4,6-trinitrobenzenesulfonic acid (TNBS) to induce colitis. Specifically, after test animals were anesthetized with ether, 0.1 ml of TNBS solution mixed with 50% ethanol was injected into the large intestine through the anus using a 1 ml syringe with a round tip, and the test animals were raised up vertically for 30 seconds to cause inflammation. Meanwhile, 0.1 ml of physiological saline was orally administered to the normal group. After the administration, the novel lactic acid bacterium *Lactobacillus mucosae* NK41, *Bifidobacterium longum* NK46 or a 1:1 mixture thereof was suspended in physiological saline which in turn was orally administered thereto in an amount of $1\times10^9$ CFU once daily for 3 days from a next day. The next day when the lactic acid bacteria administration was finished, the test animal was sacrificed, and a portion of the colon from a cecum to a site immediately before the anus was removed and then a length thereof was measured. Then, various following indicators were identified based on the length. On the other hand, 1% dextrose solution as a suspension of lactic acid bacteria instead of the novel lactic acid bacteria was administered orally to the test animals in the normal group. Further, a test animal of a positive control group was orally treated with a colitis treatment drug sulfasalazine in an amount of 50 mg/kg instead of the novel lactic acid bacteria.

(2) Measurement of Myeloperoxidase Activity

200 μl of 10 mM potassium phosphate buffer (pH 7.0) containing 0.5% hexadecyl trimethyl ammonium bromide was added to 100 mg of colon tissue, and was homogenized. The supernatant was obtained via centrifugation for 10 minutes at 4° C. and 10,000 g. 50 μl of the supernatant was added to 0.95 ml of a reaction solution (containing 1.6 mM tetramethyl benzidine and 0.1 mM $H_2O_2$) and the absorbance was measured over time at 650 nm while reacting at 37° C. The activity of myeloperoxidase (MPO) was calculated while 1 μmol/ml of $H_2O_2$ generated as a reactant was defined as one unit.

(3) Measurement of Inflammation Indicator

Western blotting methods were used to measure inflammatory response indicator materials, such as p-p65, p65, COX-2 and IL-17. Specifically, 50 μg of supernatant was obtained in the same manner as the myeloperoxidase (MPO) activity measurement test as described above and was subjected to immunoblotting. Further, the expression level of cytokines thereof was measured using an ELISA kit.

(4) Test Result

The test results performed in the above test are shown in Table 6 below.

sion levels of cytokines of TNF-α and IL-17 were suppressed, and that the activity of NF-kB and the activity of COX-2 were suppressed.

Thus, it was identified that the novel lactic acid bacterium was effective in the prevention and treatment of the colitis without showing toxicity.

Example 4: Identification of Effect of Improving Memory Using Novel Lactic Acid Bacteria Against Memory Impairment Due to Aging (1) Y-Shaped Maze Test A Y-shaped maze device used in the test had three arms extending in the shape of the alphabet Y, and each arm had a length of 25 cm, a height of 14 cm, and a width of 5 cm. An angle between adjacent arms was 120 degrees. The device was used in a short-term memory test.

Specifically, a head of the test animal was directed toward an end of one arm of the Y-shaped maze. The test animal was allowed to roam the arms freely for 8 minutes. The movement of the animal was recorded. When the animal's hind paw entered the arm, this was considered as an arm entry. The movement of animals was represented by alternation times. A single alternation time was defined as one time when the animal passed through the three arms in succession. Spontaneous alternation behavior (Spon.alternation) was expressed as a percentage between actual alternation times and maximum possible alternation times (i.e., total alternation times minus 2).

(2) Passive Avoidance Test

A passive avoidance test was conducted to evaluate long-term memory. Specifically, the mouse was placed in a brightly lit compartment (50 W light bulb), was allowed to search for 10 seconds, and then a gillotin door (5×5 cm) was opened to enter a dark compartment (Gemini Avoidance System; San Diego, USA). A time duration taken until the mouse entered the dark compartment after the gillotin door was opened was measured. This was defined as an acquisition trial. Once all four feet of the mouse entered the dark compartment, the gillotin door was closed. An electric shock

TABLE 6

| Test group | Weight change g | Colon length cm | MPO activity μU/mg | TNF-α pg/mg | IL-17 pg/mg | NF-kB activity p-p65/p65 | COX-2 activity |
|---|---|---|---|---|---|---|---|
| Normal group | 0.6 | 6.5 | 0.36 | 22 | 9 | 0.11 | 0.21 |
| Colitis-induced group | −2.5 | 4.3 | 1.79 | 185 | 52 | 0.334 | 0.56 |
| LM NK41 | −0.8 | 4.6 | 0.82 | 85 | 42 | 0.24 | 0.35 |
| BL NK46 | −0.3 | 4.8 | 0.78 | 68 | 38 | 0.27 | 0.31 |
| NK41 + NK46 | −0.5 | 5.1 | 0.79 | 82 | 39 | 0.24 | 0.32 |
| Positive group | −0.54 | 4.7 | 0.98 | 75 | 41 | 0.29 | 0.41 |

Specifically, it was identified that in a group treated with *Lactobacillus mucosae* NK41, *Bifidobacterium longum* NK46, or a mixture of thereof, there was no toxicity because a weight change was not large. Further, when the colitis was induced, the length of the colon became shorter. However, it was identified that in the group treated with the novel lactic acid bacteria, the colon length was recovered. Furthermore, in the group treated with the novel lactic acid bacteria, the increase in the myeloperoxidase activity due to the induction of colitis may be lowered. It was identified that the expresof 0.5 mA flowed through a grid bottom for 3 seconds so that the mouse remembered this situation. In order to identify the effects of the novel lactic acid bacteria, a passive avoidance test was performed 24 hours after the acquisition trial was finished. The time taken for all four feet of the mouse to enter the dark compartment after a 10-second search time and then after the gillotin door was open was measured and was defined as a latency time. While a maximum latency time was set to 300 seconds, an actual latency time was measured (retention trial).

According to the interpretation of the known test result, the longer the actual latency time, the better the memory.

(3) Water Maze Test

To test the long-term memory and spatial perception ability, a water maze test (Morris water maze test) was performed in a circular water tank containing 500 ml milk corresponding to a depth of 30 cm thereof under weak light at 20±1° C. The circular water tank had a diameter of 90 cm and a height of 45 cm. Specifically, the water tank was divided into four virtual regions, and a scaffold of 6 cm in diameter was installed in one of the four quadrants while a distance between a water top face and the scaffold was 1 cm. That is, the scaffold had a vertical level of 29 cm from a bottom of the tank. On the first day of training, swimming training was performed for 60 seconds without the scaffold, and then, for the remaining 4 days, training was performed to find the scaffold four times daily (training trial). The mouse was allowed to stay on the scaffold for 10 seconds. When the mouse could not find the scaffold for 60 seconds, the mouse was allowed to rest on the scaffold for 10 seconds. After the training was finished, the test animal was dried with a UV lamp. The training was repeated every 30 seconds. The time taken to find the scaffold was measured with a video camera. In the final test, the scaffold was removed from the water tank, and then the test animal was placed in the water tank. Then, the time spent in the target quadrant in which the scaffold was disposed was measured (probe trial).

(4) Object Recognition Test (Novel Object Test)

The object recognition test was carried out in a box (40×40×40 cm) manufactured so that the outside was not visible from the inside thereof. Objects (A, A') of the same shape and size were fixedly disposed in the box, and the mouse was started from a center of the box. The number of times the mouse touched the two objects was recorded for 10 minutes. After 24 hours, one of the two objects was replaced with a new object (A, B). Then, the number of times (exploration time) the original and new objects were touched by the mouse was recorded and calculated as a percentage.

(5) Memory Improvement Effect on Aged Animal Model

A C57BL/6 mouse (Ag, male, 19 months old) as an aged animal model was purchased from Raon Bio company to identify effects of inhibiting expression of the p16 protein as an aging factor using the novel lactic acid bacteria, and of improving memory using the novel lactic acid bacteria.

Specifically, *Lactobacillus mucosae* NK41, *Bifidobacterium longum* NK46, or a 1:1 mixture thereof was administered to the mouse at a concentration of $1\times10^9$ CFU/mouse/day for 4 weeks, respectively. Then, the Y-shaped maze test and the object recognition test of Example 3, and a measurement test of a memory-related factor in hippocampus were performed.

Figure 1:
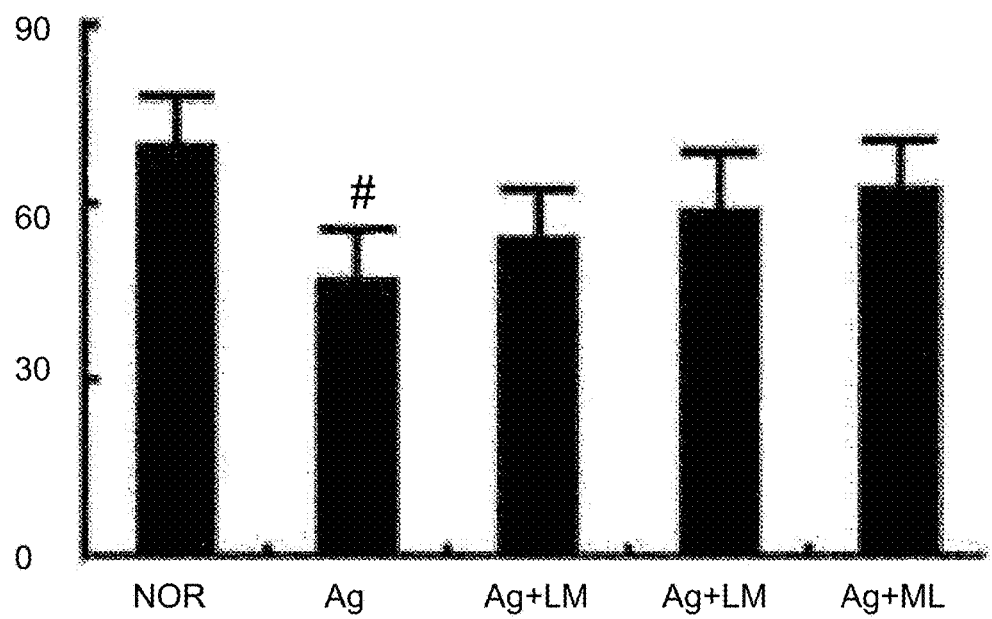
FIG. 1 shows a graph identifying that spontaneous alternation behavior is restored to a level of a normal group (NOR) in a Y-shaped maze test by administering the novel lactic acid bacterium *Lactobacillus mucosae* NK41 (LM), *Bifidobacterium longum* NK46 (BL) or a 1:1 mixture (ML) thereof to an aged animal model (Ag).
Figure 2:
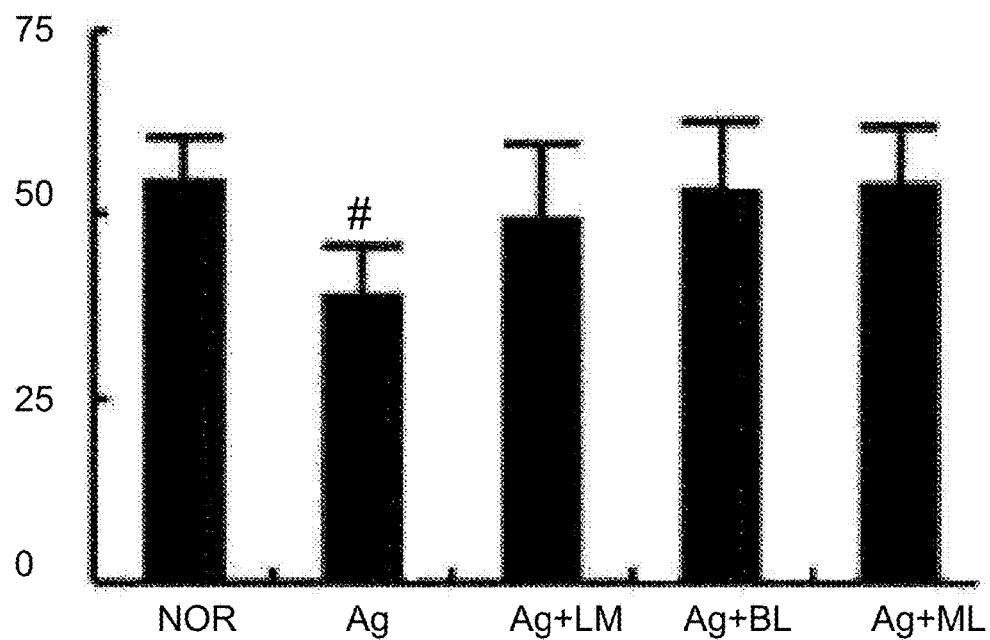
FIG. 2 shows a graph identifying that the number of times a subject touches a new object in an object recognition test is restored to a level of a normal group (NOR) by administering the novel lactic acid bacterium *Lactobacillus mucosae* NK41 (LM), *Bifidobacterium longum* NK46 (BL), or a 1:1 mixture (ML) thereof to the aged animal model (Ag).

Referring to the test results, it was identified that in the aged animal model without the lactic acid bacteria added thereto, the spontaneous alternation behavior was decreased compared to the normal group; but in the group (Ag+LM) treated with *Lactobacillus mucosae* NK41, the group (Ag+BL) treated with *Bifidobacterium longum* NK46, and the group (Ag+ML) treated with the mixture thereof, the spontaneous alternation behavior was restored to a level of the normal group (FIG. 1). Further, it was identified that in the group (Ag+ML) treated with *Lactobacillus mucosae* NK41, the group (Ag+BL) treated with *Bifidobacterium longum* NK46, and the group (Ag+ML) treated with the mixture thereof, the number of times the new object was touched was recovered to a level of the normal group (FIG. 2). It was identified that the lactic acid bacteria treated group suppressed the expression of the aging factor p16, inhibited the activity of the inflammatory factor NF-kB, and increased the expression of brain derived neurotrophic factor compared to the aged animal model (Table 7). In particular, it was identified that the mixture of *Lactobacillus mucosae* NK41 and *Bifidobacterium longum* NK46 showed better effect than the individual lactic acid bacterium.

TABLE 7

|  | P16/β-act in | BDNF/β-act in | p-p65/p65 |
|---|---|---|---|
| Normal group | 0.25 | 0.43 | 0.21 |
| Ag | 0.45 | 0.28 | 0.33 |
| Ag + LM | 0.34 | 0.34 | 0.28 |
| Ag + BL | 0.30 | 0.37 | 0.29 |
| Ag + ML | 0.29 | 0.38 | 0.27 |

Thus, it was identified that the novel lactic acid bacteria *Lactobacillus mucosae* NK41, *Bifidobacterium longum* NK46 and a mixture thereof had excellent memory improvement effect in the aged animal model.

(6) Memory Improvement Effect on Alzheimer's Disease Animal Model

The Alzheimer's disease animal model Tg mouse [B6C3-Tg (APPswe, PSEN1dE9) 85Dbo/J strain-AD mice (Jackson Laboratory, Bar Harbor, Maine, USA)] 4 months old was purchased and adapted for 2 months. A healthy C57BL/6 mouse (Orient, Seoul, Korea) of 6 months old was purchased as a normal group and adjusted for 2 months. The Tg mice were dosed with the novel lactic acid bacterium *Lactobacillus mucosae* NK41 or *Bifidobacterium longum* NK46 at a concentration of $1\times10^9$ CFU/mouse/day for 8 weeks, respectively (on Saturday and Sunday, the novel lactic acid bacterium was not administered).

Thereafter, the Y-shaped maze test, passive avoidance test, and water maze test of Example 3, and a memory-related factor measurement test in hippocampus were performed.

Figure 3:
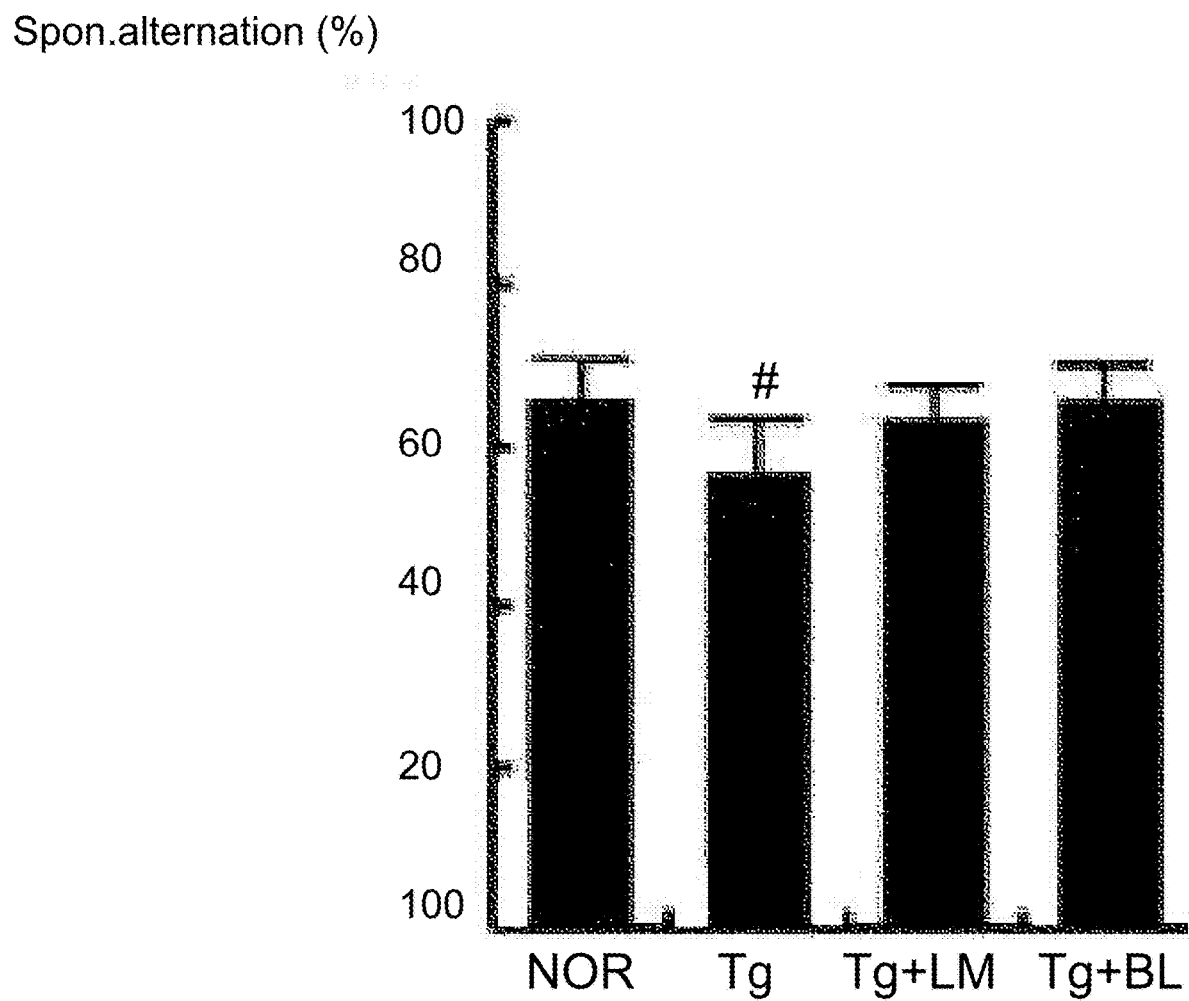
FIG. 3 shows a graph identifying that spontaneous alternation behavior is restored to a level of a normal group (NOR) in a Y-shaped maze test by administering the novel lactic acid bacterium *Lactobacillus mucosae* NK41 (LM) or *Bifidobacterium longum* NK46 (BL) to an Alzheimer's disease animal model (Tg).
Figure 4:
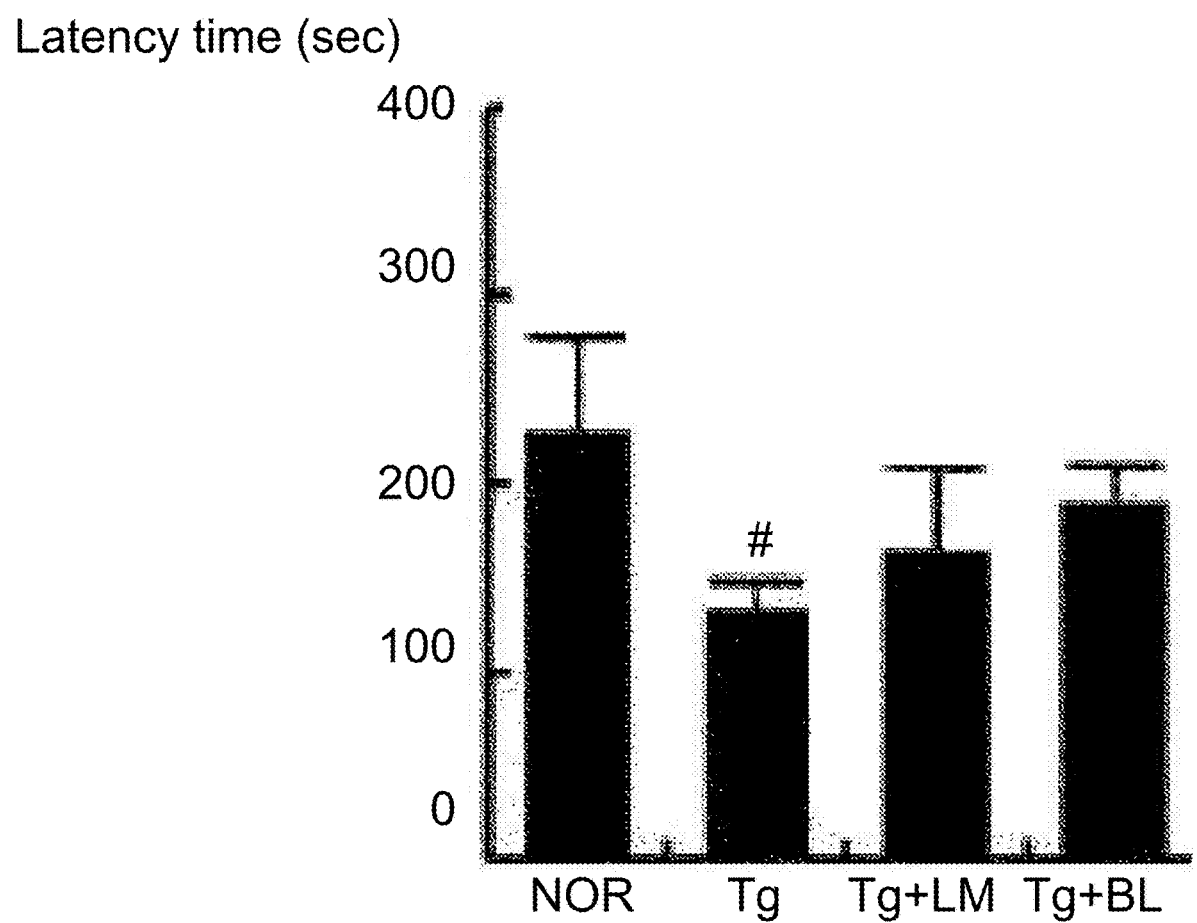
FIG. 4 shows a graph identifying that, in a passive avoidance test, a latency time is restored to a level of a normal group (NOR) via administration of the novel lactic acid bacterium *Lactobacillus mucosae* NK41 (LM) or *Bifidobacterium longum* NK46 (BL) to an Alzheimer's disease animal model (Tg).
Figure 5:
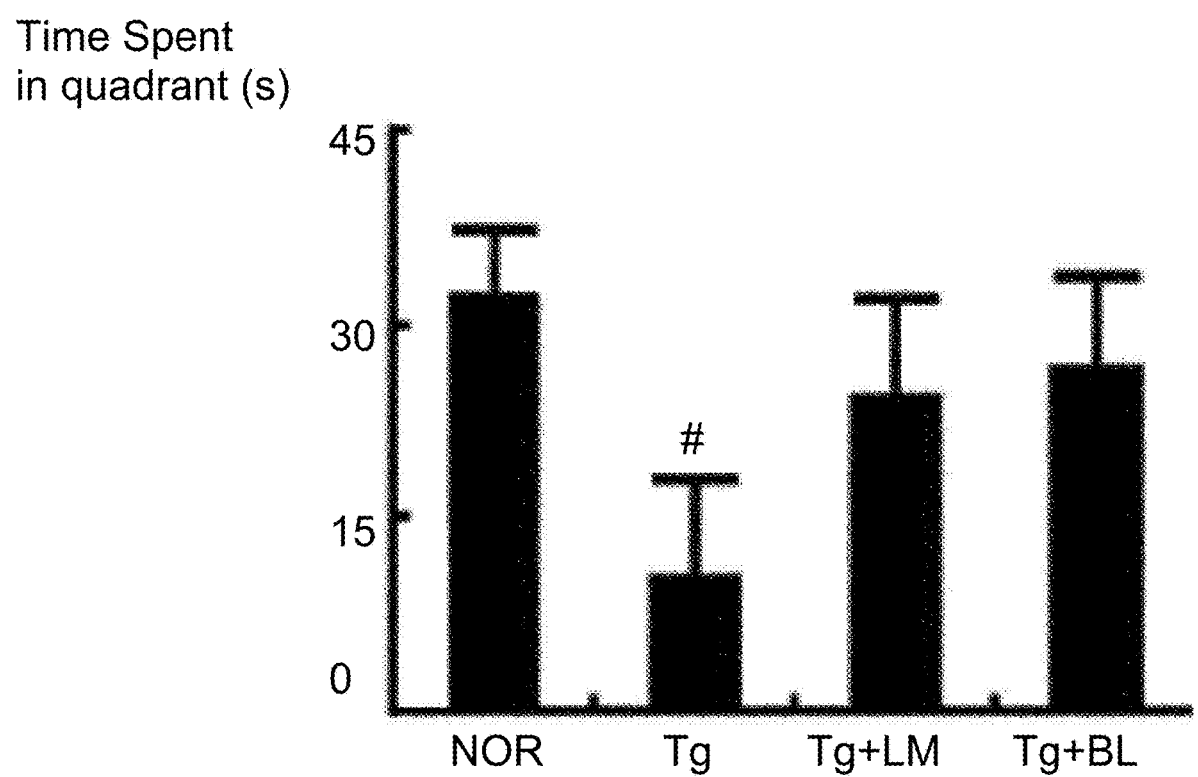
FIG. 5 shows a graph identifying that, in a water maze test, a time spent in a target quadrant is restored to a level of a normal group (NOR) via administration of the novel lactic acid bacterium *Lactobacillus mucosae* NK41 (LM) or *Bifidobacterium longum* NK46 (BL) to an Alzheimer's disease animal model (Tg).
Figure 6:
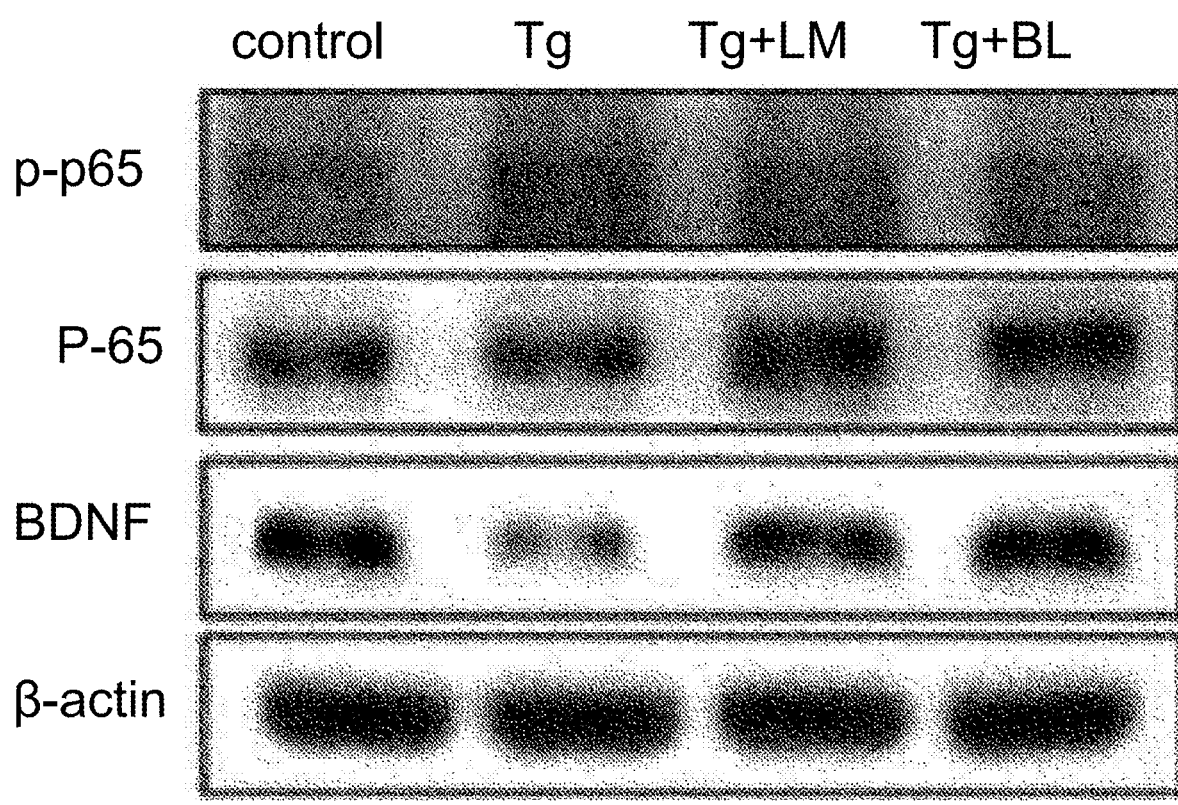
FIG. 6 shows a diagram that identifies that activity of NF-kB in hippocampus is inhibited, and expression of a brain derived neurotrophic factor (BDNF) increases, by administering the novel lactic acid bacterium *Lactobacillus mucosae* NK41 (LM) or *Bifidobacterium longum* NK46 (BL) to an Alzheimer's disease animal model (Tg).

Referring to the test results, in the Y-shaped maze test, the spontaneous alternation behavior of the Tg-mouse without the lactic acid bacteria added thereto was reduced compared to the normal group. The latency time in the passive avoidance test of the former decreased compared to the latter, and the latency time in the water maze test of the former increased compared to the latter. However, in the group (Tg+LM) treated with *Lactobacillus mucosae* NK41 and the group (Tg+BL) treated with *Bifidobacterium longum* NK46, the spontaneous alternation behavior and latency time were recovered to the levels of the normal group (FIG. 3 to FIG. 5). Further, it was identified that the lactic acid bacteria treated group had inhibited activity of NF-kB, an inflammatory factor, and had increased expression of brain derived neurotrophic factor, compared to the Tg mice (FIG. 6).

Thus, it was identified that the novel lactic acid bacterium *Lactobacillus mucosae* NK41, *Bifidobacterium longum* NK46 and a mixture thereof had excellent memory improvement effect on the Alzheimer's disease animal model.

Example 5: Effects of Novel Lactic Acid Bacteria on Mental Disorder Improvement (1) Preparation of Mental Disorder Derived Animal Model—Immobilization Stress (IS)

To induce mental disorders such as anxiety syndrome, depressed disease, or stress, the mouse was immobilized on a 3×10 cm cylindrical immobilization stress device. The immobilization stress was repeated 5 times by erecting the mouse such that a head of the mouse was directed upwardly once every 2 days. Then, anxiety behavior was measured.

(2) Elevated Plus Maze (EPM) Test

Elevated plus maze (EPM) is an experimental device for measuring the degree of mental disorders such as stress or anxiety. The elevated plus maze test device used in this test refers to a black flexi glass device having two open arms (each arm 30×7 cm) and two close arms (each arm 30×7 cm) with a wall of a height of 20 cm, in which the arms are vertically spaced from a floor by 50 cm and extended by 7 cm from a central platform. In this test, the movement of the mouse placed in the elevated plus maze in a room having a video camera at a brightness of 20 lux disposed at the top thereof was measured.

Specifically, the C57BL/6 mouse (male, 19 to 22 g) was placed in the middle of the elevated plus maze, and the head was directed toward the open arm. The time and number of times spent in the open and close arms for 5 minutes were measured. When all four feet entered the arm, an entry of the arm was counted.

The time spent in the open arm (OT) during the entire test duration was calculated as [time spent in open arm/(time spent in open arm+time spent in close arm)]×100. The open arm entry (OE) was calculated as [open arm entry/(open arm entry+close arm entry)]×100). After every behavior test, the remaining odor was removed with 70% ethanol.

According to the known interpretation of test results, when the time spent in the open arm (OT) and the open arm entry (OE) decreased, it was interpreted that mental disorder symptoms such as anxiety syndrome or depressed symptoms appeared.

(3) Test Result

Referring to the test result, after the immobilization stress was applied, in the mouse (IS) to which the lactic acid bacterium was not administered, the time spent in the open arm (OT) and the open arm entry (OE) in the elevated plus maze test decreased, compared to the normal group (NOR). However, it was identified that in the *Lactobacillus mucosae* NK41-administered group (IS+LM), *Bifidobacterium longum* NK46-administered group (IS+BL) or a 1:1 mixture thereof-administered group (IS+LM+BL), the time spent in the open arm (OT) and the open arm entry (OE) increased (Table 8).

TABLE 8

|  | Time spent in open arm (OT) % | Open arm entry (OE) % |
| --- | --- | --- |
| NOR | 15.2 | 36.2 |
| IS | 4.5 | 17.5 |
| IS + LM | 16.1 | 34.6 |
| IS + BL | 14.5 | 32.1 |
| IS + LM + BL | 16.5 | 35.8 |

Thus, the novel lactic acid bacteria *Lactobacillus mucosae* NK41 and *Bifidobacterium longum* NK46 were identified as having excellent effects of improving mental disorders such as anxiety, depression and stress.

Example 6: Improvement Effect of Depressed Syndrome Using Novel Lactic Acid Bacteria (1) Production of Depressed Mouse Model In order to induce depression disease, the mouse was fixed to a 3×10 cm cylindrical immobilization stress device, and the mouse was immobilized for 12 hours per day for 2 days such that a depressed mouse model was constructed. Thereafter, from the next day, *Lactobacillus mucosae* NK41 (LM), *Bifidobacterium longum* NK46 (BL), or a 1:1 mixture (ML) thereof was administered thereto for 5 days, and then the depressed behavior indicators were measured on the next day to the final administration day.

(2) Elevated Plus Maze (EPM) Test

The elevated plus maze test device was used in this test which is a black flexi glass device having two open arms (each arm 30×7 cm) and two close arms (each arm 30×7 cm) with a wall of a height of 20 cm, in which the arms are vertically spaced from a floor by 50 cm and extended by 7 cm from a central platform. In this test, the movement of the mouse placed in the elevated plus maze in a room having a video camera at a brightness of 20 lux disposed at the top thereof was measured.

Specifically, the C57BL/6 mouse (male, 19 to 22 g) was placed in the middle of the elevated plus maze, and the head was directed toward the open arm. The time and number of times spent in the open and close arms for 5 minutes were measured. When all four feet entered the arm, an entry of the arm was counted.

The time spent in the open arm (OT) during the entire test duration was calculated as [time spent in open arm/(time spent in open arm+time spent in close arm)]×100. After every behavior test, the remaining odor was removed with 70% ethanol.

(3) Forced Swimming Test (FST)

Based on a method as defined in Porsolts R M, Le Pichon M, Jalfre M, Nature 266: 730-732 (1977) [Depression: a new animal model sensitive to antidepressants], water at the temperature 25±1° C. was filled into the water tank having a 20 cm dimeter and 40 cm height such that the water height was 30 cm. Then, each mouse for test was placed into the water tank. Initial 2 minutes out of total 6 minutes were adaptation time for which the measurement was not made. Then, the test animal immobility time during the next 4 minutes was measured. The immobile state refers to a floating state over the water while standing upright at a minimal movement amount to expose only the head to air out of the water. When the depressed state was reduced, the reduction of the immobile state was exhibited.

(4) Tail Suspension Test (TST)

Based on a method defined in Stem, L. et al., Psycho-pharmacology, (1985) 85, 367-370, [The tail suspension test: a new method for screening antidepressants in mice.], a fixing device was mounted to a 1 cm position from a tip end of a tail of the mouse. The mouse was suspended at a position spaced by 50 cm upwardly from a ground, and the immobility time of the test animals was measured for a total of 6 minutes.

(5) Measurement of Anxiety and Depression Symptom Markers

As in the above item (1), the depressed mouse model was produced by applying immobilization stress thereto. *Lactobacillus mucosae* NK41 (LM), *Bifidobacterium longum* NK46 (BL), or a 1:1 mixture (ML) thereof was administered thereto for 5 days, and then, anxiety and depression symptom markers were measured the next day to the final administration day.

Corticosterone in mouse blood was measured by an enzyme-linked immunosorbent assay (ELISA) kit (Ebiosci-ence, San Diego, California). BDNF (Brain-derived neurotrophic factor) and NF-kB (p-p65, p65) were measured using the immunoblotting method.

Specifically, hippocampus was surgically removed. RIPA lysis buffer containing 1% protease inhibitor cocktail and phosphatase inhibitor cocktail was added thereto. Homogenization was uniformly performed, followed by centrifugation (13,200×g, 10 min, 4° C.) to obtain a supernatant. The supernatant was electrophoresed in a 12% SDS (sodium dodecyl sulfate-polyacrylamide) gel, and then was transferred to a nitrocellulose membrane, and then was blocked with a skim milk protein, and was washed. Subsequently, the washed product was treated with BDNF, p65, p-p65, and β-Actin antibodies which were coupled thereto. Then, the treated product was washed, and treated with a secondary antibody containing horseradish peroxidase. Then, proteins were identified using an enhanced chemiluminescence detection kit.

(6) Fluorescence Immunostaining

The brain slices were fixed on a slide glass and were treated with anti-Iba1 (ionized calcium-binding adapter molecule 1) antibody (1:100, Abcam) or DAPI (4',6-diamidino-2-phenylindole) according to a method disclosed from Lee et al. The microglia was identified using a confocal microscope.

(7) Test Result

As shown in FIG. 7, after induction of the depression disease, in the mice (DC) without administration of the lactic acid bacteria added thereto, the time spent in the open arm (OT) and the open arm entry (OE) in the elevated plus maze test decreased, compared to normal group (NOR). However, it was identified that in the group (DC+LM) treated with *Lactobacillus mucosae* NK41, the group (DC+BL) treated with *Bifidobacterium longum* NK46, or the group (DC+ML) treated with a 1:1 mixture thereof, the time spent in the open arm (OT) and the open arm entry (OE) increased.

Thus, the novel lactic acid bacteria *Lactobacillus mucosae* NK41, *Bifidobacterium longum* NK46, and a mixture thereof were identified as having excellent depression symptom reduction effect.

As shown in FIG. 8, it was identified that the anxiety behavior and depression symptoms caused by immobilization stress in the forced swimming test were reduced due to the decrease in the immobility in the group (DC+LM) treated with *Lactobacillus mucosae* NK41, the group (DC+BL) treated with *Bifidobacterium longum* NK46, or the group (DC+ML) treated with a 1:1 mixture thereof.

As shown in FIG. 9, it was identified that the anxiety behavior and depression symptoms induced by immobilization stress in the tail suspension test were reduced due to the decrease in the immobility in the group (DC+LM) treated with *Lactobacillus mucosae* NK41, the group (DC+BL) treated with *Bifidobacterium longum* NK46, or the group (DC+ML) treated with a 1:1 mixture thereof.

As shown in FIG. 10, in the hippocampus of the depressed mouse model induced by immobilization stress, the expression of brain derived neurotrophic factor (BDNF) was reduced, and NF-kB activity was induced. On the other hand, it was identified that the expression of brain derived neurotrophic factor (BDNF) increased, and NF-kB activity was inhibited in the group (DC+LM) treated with *Lactobacillus mucosae* NK41, the group (DC+BL) treated with *Bifidobacterium longum* NK46, or the group (DC+ML) treated with a 1:1 mixture thereof.

Further, as shown in FIG. 11, when measuring corticosterone in the blood, in the depressed mouse model, corticosterone increased significantly. However, it was identified that the corticosterone in the blood was significantly reduced in the group (DC+LM) treated with *Lactobacillus mucosae* NK41, the group (DC+BL) treated with *Bifidobacterium longum* NK46, or the group (DC+ML) treated with a 1:1 mixture thereof.

In addition, when observing Iba1-positive activated microglia in the hippocampus, as shown in FIG. 12, in the depressed mouse model, activation of Iba1 positive microglia was observed in both CA1 and CA3 regions of hippocampus. However, it was identified that the activation of Iba1 and microglia as observed in both CA1 and CA3 regions of hippocampus significantly decreased in the group (DC+LM) treated with *Lactobacillus mucosae* NK41, the group (DC+BL) treated with *Bifidobacterium longum* NK46, or the group (DC+ML) treated with a 1:1 mixture thereof.

From the above results, the novel lactic acid bacteria *Lactobacillus mucosae* NK41 and *Bifidobacterium longum* NK46 were identified as having excellent reducing effect of the depressed symptoms and anxiety symptoms.

<Deposition Information of Lactic Acid Bacteria>

The present inventors have deposited a patent of *Lactobacillus mucosae* NK41 on Aug. 4, 2017 into the Korean Culture Center of Microorganisms as an accredited depositary organization (Address: Yurim Building, 45, 2-ga-gil, Hongjenae, Seodaemun-gu, Seoul, Korea), and thus an accession number, KCCM12091P, was assigned.

Further, the present inventors have deposited a patent of *Bifidobacterium longum* NK46 on Aug. 4, 2017 into the Korean Culture Center of Microorganisms as an accredited depositary organization (Address: Yurim Bldg, 45, 2-ga-gil, Hongjenae, Seodaemun-gu, Seoul, Korea), and thus an accession number, KCCM12087P, was assigned.

Depository name: Korean Culture Center of Microorganisms (Overseas)

Accession number: KCCM12087P

Date of Deposit: Aug. 4, 2017

Depository name: Korean Culture Center of Microorganisms (Overseas)

Accession number: KCCM12091P

Date of Deposit: Aug. 4, 2017

The ASCII text file "Sequence.txt" created on Oct. 7, 2020, having the size of 5 KB, is incorporated by reference into the specification.

What is claimed is:

1. A method for treating memory impairment, learning disability or mental disorder disease in a subject in need thereof, comprising administering to the subject a therapeutically effective amount of a composition comprising *Bifidobacterium longum* NK46 (accession number: KCCM12087P).

2. The method of claim 1, wherein the *Bifidobacterium longum* NK46 (accession number: KCCM12087P) comprises the 16S rDNA base sequence of SEQ ID NO:2.

3. The method of claim 1, wherein the memory impairment or the learning disability is at least one selected from the group consisting of aging, Alzheimer's disease, schizophrenia, Parkinson's disease, Huntington's disease, Pick's disease, Creutzfeldt-Jakob disease, head trauma, forgetfulness, memory power decrease, traumatic brain injury, epilepsy, hippocampal sclerosis, headache, cerebral senile disease, dementia, and memory loss.

4. The method of claim 1, wherein the mental disorder is at least one selected from the group consisting of anxiety, depressed symptoms, mood disorders, insomnia, delusional disorder, obsessive compulsive disorder, migraine, stress, cognitive disorder, and attention disorder.

5. The method of claim 1, wherein the *Bifidobacterium longum* NK46 (accession number: KCCM12087P) suppresses expression of p16 protein as an aging factor.

6. The method of claim 1, wherein the *Bifidobacterium longum* NK46 (accession number: KCCM12087P) is a live probiotic thereof, a heat killed probiotic thereof, a culture thereof, a lysate thereof or an extract thereof.

* * * * *

SEQUENCE LISTING

```
<160> NUMBER OF SEQ ID NOS: 2

<210> SEQ ID NO 1
<211> LENGTH: 1513
<212> TYPE: DNA
<213> ORGANISM: Artificial Sequence
<220> FEATURE:
<223> OTHER INFORMATION: NK41 16s rDNA

<400> SEQUENCE: 1
```

-continued

| | |
|---|---|
| agattcaccc taatcatctg ccccaccttaa ggcggctagc tccccgaagg gttacccacc | 60 |
| cgactttggg tgttgcaaac tctcatggtg tgacgggcgg tgtgtacaag gccccgggaa | 120 |
| cgtatttcca cccgggcatg ctgatccgcg attactagcg attccgactt cgtgcaggcg | 180 |
| agttgcagcc tgcagtccga actgagaacg gttttaagag attagcttgc cctcgcgagt | 240 |
| tcgcgactcg ttgtaccgtc cattgtagca cgtgtgtagc ccaggtcata aggggcatga | 300 |
| tgatctgacg tcgtccccac cttcctccgg tttgtcaccg gcagtctcac tagagtgccc | 360 |
| aactgaatgc tggcaactag taacaagggt tgcgctcgtt gcgggactta acccaacatc | 420 |
| tcacgcacg agctgacgac gaccatgcac cacctgtcat tgcgttcccg aaggaaacgc | 480 |
| cctatctcta gggttggcgc aagatgtcaa gacctggtaa ggttcttcgc gtagcttcga | 540 |
| attaaaccac atgctccacc gcttgtgcgg gccccgtca attcctttga gtttcaacct | 600 |
| tgcggtcgta ctccccaggc ggagtgctta atgcgttagc tgcggcactg aagggcggaa | 660 |
| accctccaac acctagcact catcgtttac ggcatggact accagggtat ctaatcctgt | 720 |
| tcgctaccca tgctttcgag cctcagcgtc agttgcagac cagacagccg ccttcgccac | 780 |
| tggtgttctt ccatatatct acgcattcca ccgctacaca tggagttcca ctgtcctctt | 840 |
| ctgcactcaa gtctgacagt ttccgatgca cttctttggt taagccaaag ctttcacat | 900 |
| cagacttatc aaaccgcctg cgctcgcttt acgcccaata aatccggata acgcttgcca | 960 |
| cctacgtatt accgcggctg ctggcacgta gttagccgtg actttctggt tagataccgt | 1020 |
| cactgcgtga acagttgctc tcacgcacgt tcttctctaa caacagagct ttacgagccg | 1080 |
| aaacccttct tcactcacgc ggtgttgctc catcaggctt gcgcccattg tggaagattc | 1140 |
| cctactgctg cctcccgtag gagtatggac cgtgtctcag ttccattgtg gccgatcagt | 1200 |
| ctctcaactc ggctacgcat cacagccttg gtaggccgtt accctaccaa caagctaatg | 1260 |
| cgccgcaggt ccatcccaaa gtgatagccg aagccatctt ttaaatttga atcatgcgat | 1320 |
| tcaaattgtt atgcggtatt agcatctgtt tccaaatgtt atcccccgct ttggggcagg | 1380 |
| ttacctacgt gttactcacc cgtccgccac tcgctggtaa accaacgtca agtccgtgca | 1440 |
| agcacgttca atcagttggg ccaacgcgtt cgacttgcat gtattaggca caccgccggc | 1500 |
| gttcatcctg agc | 1513 |

<210> SEQ ID NO 2
<211> LENGTH: 1469
<212> TYPE: DNA
<213> ORGANISM: Artificial Sequence
<220> FEATURE:
<223> OTHER INFORMATION: NK46 16s rDNA

<400> SEQUENCE: 2

| | |
|---|---|
| tttacccctg ttacgactta gtcccaatca cgagcctcac cttagacggc tccatcccac | 60 |
| aaggggttag gccaccggct tcgggtgctg cccacttca tgacttgacg ggcggtgtgt | 120 |
| acaaggcccg ggaacgcatt caccgcgacg ttgctgattc gcgattacta gcgactccgc | 180 |
| cttcacgcag tcgagttgca gactgcgatc cgaactgaga ccggttttca gggatccgct | 240 |
| ccgcgtcgcc gcgtcgcatc ccgttgtacc ggccattgta gcatgcgtga agccctggac | 300 |
| gtaaggggca tgatgatctg acgtcatccc caccttcctc cgagttaacc ccggcggtcc | 360 |
| cccgtgagtt cccggcataa tccgctggca acacggggcg agggttgcgc tcgttgcggg | 420 |
| acttaacccaa acatctcacg acacgagctg acgacgacca tgcaccacct gtgaacccgc | 480 |
| cccgaaggga agccgcatct ctacgaccgt cgggaacatg tcaagcccag gtaaggttct | 540 |

```
tcgcgttgca tcgaattaat ccgcatgctc cgccgcttgt gcgggccccc gtcaatttct      600
ttgagtttta gccttgcggc cgtactcccc aggcgggatg cttaacgcgt tagctccgac      660
acggaacccg tggaacgggc cccacatcca gcatccaccg tttacggcgt ggactaccag      720
ggtatctaat cctgttcgct ccccacgctt tcgctcctca gcgtcagtaa cggcccagag      780
acctgccttc gccattggtg ttcttcccga tatctacaca ttccaccgtt acaccgggaa      840
ttccagtctc ccctaccgca ctcaagcccg cccgtacccg gcgcggatcc accgttaagc      900
gatggacttt cacaccggac gcgacgaacc gcctacgagc cctttacgcc caataattcc      960
ggataacgct tgcaccctac gtattaccgc ggctgctggc acgtagttag ccggtgctta     1020
ttcaacgggt aaactcactc tcgcttgctc cccgataaaa gaggtttaca acccgaaggc     1080
ctccatccct cacgcggcgt cgctgcatca ggcttgcgcc cattgtgcaa tattccccac     1140
tgctgcctcc cgtaggagtc tgggccgtat ctcagtccca atgtggccgg tcgccctctc     1200
aggccggcta cccgtcgaag ccacggtggg ccgttacccc gccgtcaagc tgataggacg     1260 cgacccatc ccataccgcg aaagctttcc cagaagacca tgcgatcaac tggagcatcc     1320
ggcattacca cccgtttcca ggagctattc cggtgtatgg ggcaggtcgg tcacgcatta     1380 ctcaccgtt cgccactctc accaccaagc aaagcctgat ggatcccgtt cgacttgcat     1440
gtgttaagca cgccgccagc gttcatcct                                      1469
```